(12) United States Patent
Sagatelyan

(10) Patent No.: US 7,227,128 B2
(45) Date of Patent: Jun. 5, 2007

(54) SYSTEM AND METHODS FOR IMPROVING SIGNAL/NOISE RATIO FOR SIGNAL DETECTORS

(75) Inventor: Dmitry M. Sagatelyan, Alameda, CA (US)

(73) Assignee: Applera Corporation, Foster City, CA (US)

( * ) Notice: Subject to any disclaimer, the term of this patent is extended or adjusted under 35 U.S.C. 154(b) by 2 days.

(21) Appl. No.: 11/173,113

(22) Filed: Jun. 30, 2005

(65) Prior Publication Data

US 2007/0001117 A1   Jan. 4, 2007

(51) Int. Cl.
    *G12B 13/00* (2006.01)
(52) U.S. Cl. .................... 250/252.1; 250/300
(58) Field of Classification Search ........... 250/300, 250/341.5, 252.1
    See application file for complete search history.

(56) References Cited

U.S. PATENT DOCUMENTS

| | | | |
|---|---|---|---|
| 5,014,216 A * | 5/1991 | Stafford et al. ............... | 702/25 |
| 5,401,465 A | 3/1995 | Smethers et al. | |
| 5,715,048 A | 2/1998 | Taylor | |
| 6,531,691 B1 | 3/2003 | Pruet et al. | |
| 6,738,502 B1 | 5/2004 | Coleman et al. | |
| 6,759,235 B2 * | 7/2004 | Empedocles et al. .... | 435/288.7 |
| 2002/0090650 A1 * | 7/2002 | Empedocles et al. ........ | 435/7.1 |
| 2003/0165398 A1 | 9/2003 | Waldo et al. | |
| 2005/0272046 A1 * | 12/2005 | Schermer et al. .............. | 435/6 |
| 2006/0133564 A1 * | 6/2006 | Langan et al. ................. | 378/8 |

OTHER PUBLICATIONS

Operation Manual for LS100 Thermal Imager, SPECTRALINE Document No. LS1001 Version 1.01 dated Nov. 11, 2002 (entire document).
Copy of International Search Report for International application No. PCT/US06/25367 dated Mar. 1, 2007, along with Written Opinion of the International Searching Authority.

* cited by examiner

*Primary Examiner*—David Porta
*Assistant Examiner*—Christine Sung

(57) ABSTRACT

A method and system for characterizing and quantifying various error and calibration components of signals associated with photo-detectors. By varying the detector operational parameters such as input light intensity and integration times, measured signals can be analyzed to separate out and quantify various components of the measured signals. The various components thus determined may be categorized according to their dependencies on the operational parameters. Such component characterization allows better understanding of the detector system and ways in which such system can be improved so as to yield an improved measurement result for which the detector is being utilized.

57 Claims, 21 Drawing Sheets

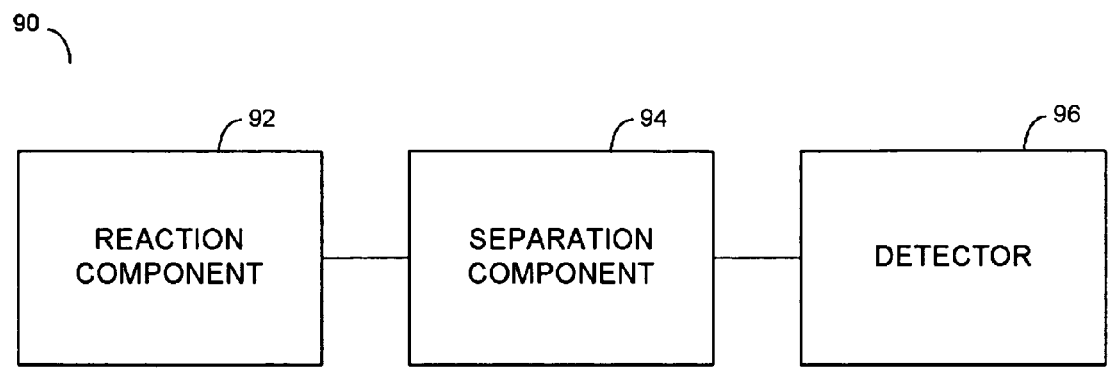
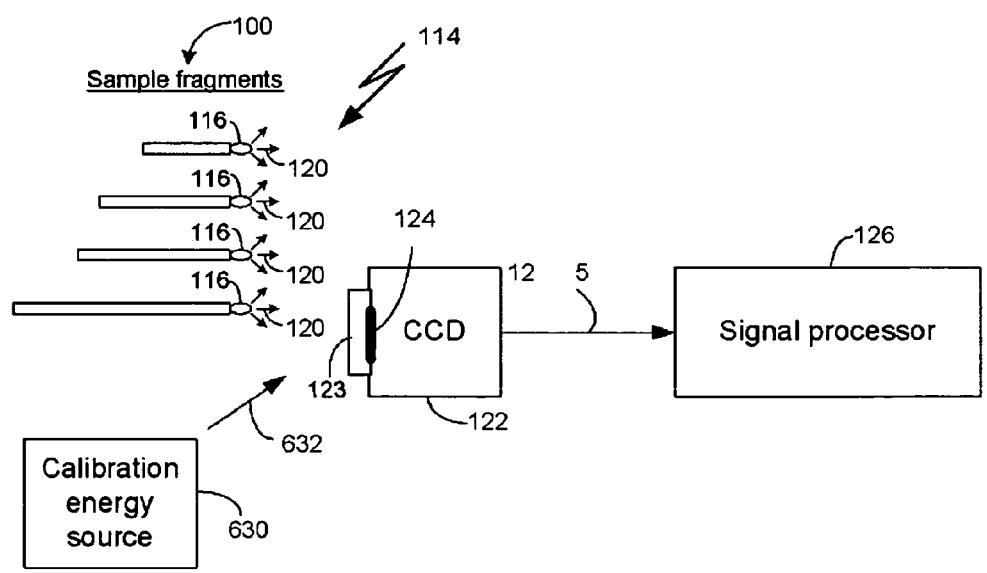

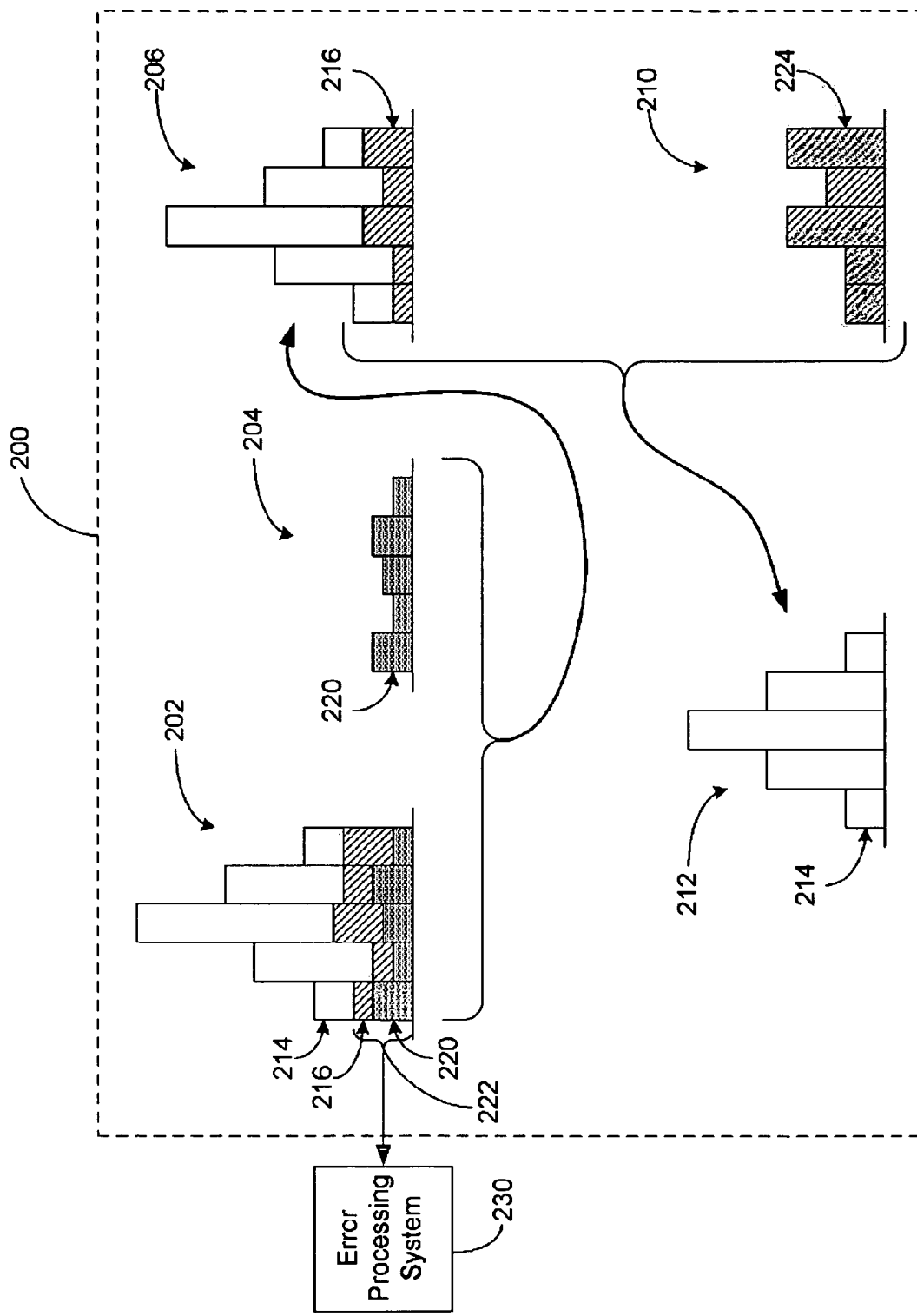

762

SYSTEM AND METHODS FOR IMPROVING SIGNAL/NOISE RATIO FOR SIGNAL DETECTORS

BACKGROUND

1. Field

The present teachings generally relate to the field of signal processing and more particularly, to a system and methods for detecting and resolving signals associated with a biological analysis platform.

2. Description of the Related Art

During biological analysis, such as nucleotide sequencing or microarray processing, photo-detectors such as charge coupled devices (CCD) are used to detect signals arising from labeled samples or probe features responsive to selected target analytes. These signals may take the form of fluorescent or visible light emissions that are desirably analyzed to quantify observed light intensity arising from each labeled sample or probe feature and are subsequently resolved to quantitatively or qualitatively evaluate the presence of a target analyte within a sample. Generally, the photo detector, used in the analysis, comprises a segmented array of light-detecting elements or pixels. During image acquisition, systematic errors inherent in the detector and/or undesirable deviations or variability induced by the operating conditions of the instrument may confound accurate resolution of the signals. The effects of these deviations and variability may manifest themselves as a "black box" like error that may reduce accuracy and sensitivity in data acquisition and induce undesirable variability in the analysis results. Consequently, there is an ongoing need for an improved approach in which photo-detector related errors are identified and characterized to improve the overall quality of data acquisition in biological analysis.

SUMMARY

One aspect of the present teachings relates to a method of performing a biological assay using a detector comprising a plurality of pixel elements configured to resolve signal emissions arising from a biological sample. The method comprises evaluating a plurality of response signals generated by each of the pixel elements resulting from exposure to a calibration signal while varying the intensity of the calibration signal in combination with varying of an acquisition time of the pixel elements. The method further comprises identifying systematic signal deviations in the detector and normalizing pixel element response by comparison of the response signals generated while varying the calibration signal intensity and acquisition time. The method further comprises applying the systematic signal deviations and the pixel normalization to a measured raw data corresponding to the emitted signal from the biological sample. The response signals that yield the systematic signal deviations and the pixel normalization are obtained in a similar condition as that of the measured raw data.

In certain implementations, the method further comprises directing a calibration signal towards the detector such that each of the plurality of pixel elements is exposed to the calibration signal in a substantially uniform manner for the acquisition time.

In certain implementations, the variations in calibration signal intensity comprise a first and second signal intensity. The variations in pixel element acquisition time comprise a first and second signal acquisition time thereby allowing determination of four or less components of a given response signal.

In one implementation, the first signal intensity comprises a substantially uniform non-zero intensity and the second signal intensity comprises a substantially nil intensity. The first signal acquisition time comprises a long signal acquisition time and the second signal acquisition time comprises a short signal acquisition time. The long acquisition time is greater than the short acquisition time.

In such an implementation, the four components of a given response signal comprises a first component that depends on both the calibration signal intensity and the acquisition time; a second component that depends on the calibration signal intensity but not on the acquisition time; a third component that depends on the acquisition time but not on the calibration signal intensity; and a fourth component that depends neither on the calibration signal intensity or the acquisition time.

In such an implementation, the first component comprises a baseline component suitable for flat-field correction. The second component comprises a contribution to the response signal when the calibration signal intensity transitions from the non-zero intensity to the substantially nil intensity. The third component comprises a dark signal component. The fourth component comprises a contribution to the response signal during an idle period following the acquisition time.

In one implementation, applying the systematic signal deviations and the pixel normalization comprises the steps of subtracting the idle period contribution from the measured raw data to yield a first adjusted data for a given pixel; subtracting the dark signal component from the first adjusted data to yield a second adjusted data for the pixel; removing the calibration signal intensity transition contribution from the second adjusted data to yield a third adjusted data for the pixel; and normalizing the third adjusted data of the given pixel relative to other pixels by comparing the given pixel's baseline component to that of the other pixels wherein the normalization of the third adjusted data yields a fourth adjusted data.

In one implementation, identifying systematic signal deviations comprises steps of obtaining, for each pixel, measured raw data comprising a baseline long signal value $A_{BL}$ during a known long measurement frame duration $T_{PL}$, a baseline short signal value $A_{BS}$ during a known short measurement frame duration $T_{PS}$, a dark long signal value $A_{DL}$ during another $T_{PL}$, and a dark short signal value $A_{DS}$ during another $T_{PS}$; determining, for each pixel, signal values $W_{ie}$ and $W_{DC}$ corresponding to the baseline component and the dark signal component, respectively, based on the measured and known values $A_{BL}$, $A_{BS}$, $A_{DL}$, $A_{DS}$, $T_{PL}$, and $T_{PS}$; determining, for each pixel having an indices i and j, time durations $T_L$, $T_S$, $T_{idle}$, and $T_{ns}^{ij}$ corresponding to time values of long acquisition time, short acquisition time, idle time, and the calibration signal intensity transition time, respectively, based on the determined or known values $A_{BL}$, $A_{BS}$, $A_{DL}$, $A_{DS}$, $T_{PL}$, $T_{PS}$, and a ratio of long and short acquisition times; and determining, for each pixel, the calibration signal components based on the determined or known values $A_{BL}$, $A_{BS}$, $A_{DL}$, $A_{DS}$, $T_{PL}$, $T_{PS}$, $T_L$, $T_S$, $T_{idle}$, $T_{ns}^{ij}$, $W_{ie}$, and $W_{DC}$.

In such an implementation, determining the aforementioned values comprise $W_{ie}=[(A_{BL}-A_{BS})-(A_{DL}-A_{DS})]/(T_{PL}-T_{PS})$; $W_{DC}=(A_{DL}-A_{DS})/(T_{PL}-T_{PS})$; $T_L=n(T_{PL}-T_{PS})/(n-1)$ where n is representative of a ratio of long and short acquisition times; $T_S=T_L-(T_{PL}-T_{PS})$; $T_{idle}=(nT_{PS}-T_{PL})/(n-1)$; $T_{ns}^{ij}=(n-m^{ij})(T_{PL}-T_{PS})/[(m^{ij}-1)(n-1)]$ where $m^{ij}=(A_{BL}-$ $A_{DL})/(A_{BS}-A_{DS})$; $A_{L1}=W_{ie} T_L$ is representative of the long baseline component suitable for flat-field correction; $A_{S1}=W_{ie} T_S$ is representative of the short baseline component; $A_2=W_{ie} T_{ns}^{ij}$ is representative of the contribution during the calibration signal intensity transition time for both long and short acquisition times; $A_{L3}=W_{DC} T_L$ is representative of the dark signal component during the long acquisition time; $A_{S3}=W_{DC} T_S$ is representative of the dark signal component during the short acquisition time; and $A_2=A_{DL}-A_{L3}$ is representative of the contribution during the idle time.

Another aspect of the present teachings relates to a system for performing a biological assay. The system comprises a biological sample configured to emit signals, and a detector comprising a plurality of pixel elements configured to resolve the emitted signals from the biological sample. The system further comprises a processor configured to acquire and evaluate response signals from the pixel elements generated by each of the pixel elements resulting from exposure to a calibration signal while varying the intensity of the calibration signal in combination with varying of an acquisition time of the pixel elements. The processor is further configured to identify systematic signal deviations in the detector and normalize pixel element response by comparison of the response signals generated while varying the calibration signal intensity and acquisition time. The processor applies the systematic signal deviations and the pixel normalization to a measured raw data corresponding to the emitted signal from the biological sample. The response signals that yield the systematic signal deviations and the pixel normalization are obtained in a similar condition as that of the measured raw data.

In certain embodiments, the system further comprises a calibration component configured to direct a calibration signal towards the detector such that each of the plurality of pixel elements is exposed to the calibration signal in a substantially uniform manner for a predetermined acquisition time to generate a plurality of response signals.

In certain embodiments, the variations in calibration signal intensity comprise a first and second signal intensity. The variations in pixel element acquisition time comprise a first and second signal acquisition time thereby allowing determination of four or less components of a given response signal.

In one embodiment, the first signal intensity comprises a substantially uniform non-zero intensity and the second signal intensity comprises a substantially nil intensity. The first signal acquisition time comprises a long signal acquisition time and the second signal acquisition time comprises a short signal acquisition time. The long acquisition time is greater than the short acquisition time.

In such an embodiment, the four components of a given response signal comprises a first component that depends on both the calibration signal intensity and the acquisition time; a second component that depends on the calibration signal intensity but not on the acquisition time; a third component that depends on the acquisition time but not on the calibration signal intensity; and a fourth component that depends neither on the calibration signal intensity or the acquisition time.

In such an embodiment, the first component comprises a baseline component suitable for flat-field correction. The second component comprises a contribution to the response signal when the calibration signal intensity transitions from the non-zero intensity to the substantially nil intensity. The third component comprises a dark signal component. The fourth component comprises a contribution to the response signal during an idle period following the acquisition time.

In one embodiment, the processor applies the systematic signal deviations and the pixel normalization by subtracting the idle period contribution from the measured raw data to yield a first adjusted data for a given pixel; subtracting the dark signal component from the first adjusted data to yield a second adjusted data for the pixel; removing the calibration signal intensity transition contribution from the second adjusted data to yield a third adjusted data for the pixel; and normalizing the third adjusted data of the given pixel relative to other pixels by comparing the given pixel's baseline component to that of the other pixels wherein the normalization of the third adjusted data yields a fourth adjusted data.

In one embodiment, the processor identifies systematic signal deviations by obtaining, for each pixel, measured raw data comprising a baseline long signal value $A_{BL}$ during a known long measurement frame duration $T_{PL}$, a baseline short signal value $A_{BS}$ during a known short measurement frame duration $T_{PS}$, a dark long signal value $A_{DL}$ during another $T_{PL}$, and a dark short signal value $A_{DS}$ during another $T_{PS}$; determining, for each pixel, signal values $W_{ie}$ and $W_{DC}$ corresponding to the baseline component and the dark signal component, respectively, based on the measured and known values $A_{BL}$, $A_{BS}$, $A_{DL}$, $A_{DS}$, $T_{PL}$, and $T_{PS}$; determining, for each pixel having indices i and j, time durations $T_L$, $T_S$, $T_{idle}$, and $T_{ns}^{ij}$ corresponding to time values of long acquisition time, short acquisition time, idle time, and the calibration signal intensity transition time, respectively, based on the determined or known values $A_{BL}$, $A_{BS}$, $A_{DL}$, $A_{DS}$, $T_{PL}$, $T_{PS}$, and a ratio of long and short acquisition times; and determining, for each pixel, the calibration signal components based on the determined or known values $A_{BL}$, $A_{BS}$, $A_{DL}$, $A_{DS}$, $T_{PL}$, $T_{PS}$, $T_L$, $T_S$, $T_{idle}$, $T_{ns}^{ij}$, $W_{ie}$, and $W_{DC}$.

In such an embodiment, determining the aforementioned values comprise $W_{ie}=[(A_{BL}-A_{BS})-(A_{DL}-A_{DS})]/(T_{PL}-T_{PS})$; $W_{DC}=(A_{DL}-A_{DS})/(T_{PL}-T_{PS})$; $T_{L=n(TPL}-T_{PS})/(n-1)$ where n is representative of a ratio of long and short acquisition times; $T_S=T_L-(T_{PL}-T_{PS})$; $T_{idle}=(nT_{PS}-T_{PL})/(n-1)$; $T_{ns}^{ij}=(n-m^{ij})(T_{PL}-T_{PS})/[(m^{ij}-1)(n-1)]$ where $m^{ij}=(A_{BL}-A_{DL})/(A_{BS}-A_{DS})$; $A_{L1}=W_{ie} T_L$ is representative of the long baseline component suitable for flat-field correction; $A_{S1}=W_{ie} T_S$ is representative of the short baseline component; $A_2=W_{ie} T_{ns}^{ij}$ is representative of the contribution during the calibration signal intensity transition time for both long and short acquisition times; $A_{L3}=W_{DC} T_L$ is representative of the dark signal component during the long acquisition time; $A_{S3}=W_{DC} T_S$ is representative of the dark signal component during the short acquisition time; and $A_2=A_{DL}-A_{L3}$ is representative of the contribution during the idle time.

Another aspect of the present teachings relates to a system for characterizing a detector for a biological analyzer. The system includes a processor configured to acquire and evaluate signals from the detector resulting from exposure to a calibration signal while varying the intensity of the calibration signal in combination with varying of acquisition time of the detector. The processor is configured to resolve the response signal, based on the variations in the intensity of the calibration signal and the acquisition time, into two or more components that contribute to the response signals.

In one embodiment, the system further includes a calibration component configured to direct a calibration signal towards the detector such that at least a portion of the detector is exposed to the calibration signal in a substantially uniform manner for a predetermined acquisition time to generate a response signal.

In one embodiment, the detector includes a plurality of pixel elements. A portion or substantially all of such a detector can be characterized. In one embodiment, the detector is a charge coupled device. In one embodiment, the response signal from the detector includes a plurality of signals corresponding to the plurality of pixels. The pixel signals can be processes so that each pixel is characterized. The pixels can also be grouped into bins, so that a signal from each bin represents a combination of signals from the pixels in that bin.

In one embodiment, the variations in calibration signal intensity include a first and a second signal intensity. The variations in detector acquisition time include a first and a second signal acquisition time thereby allowing determination of two to four components of a given response signal. In one embodiment, the first signal intensity includes a substantially uniform non-zero intensity and the second signal intensity includes a substantially nil intensity. In one embodiment, the first acquisition time includes a long signal acquisition time and the second acquisition time includes a short signal acquisition time. The long acquisition time is greater than the short acquisition time. In one embodiment, four components are resolved for a given response signal: (a) a first component that depends on both the calibration signal intensity and the acquisition time; (b) a second component that depends on the calibration signal intensity but not on the acquisition time; (c) a third component that depends on the acquisition time but not on the calibration signal intensity; and (d) a fourth component that depends neither on the calibration signal intensity or the acquisition time.

In one embodiment where such four components are resolved, first component includes a baseline component. The second component includes a contribution to the response signal when the calibration signal intensity transitions from the non-zero intensity to the substantially nil intensity. The third component includes a dark signal component. The fourth component includes a contribution to the response signal during an idle period following the acquisition time.

Another aspect of the present teachings relates to a method characterizing a detector for a biological analyzer. The method includes evaluating a response signal while varying the intensity of a calibration signal in combination with varying of an acquisition time. The method further includes resolving the response signal based on the variations in the intensity of the calibration signal and the acquisition time, into two or more components that contribute to the response signal.

In one embodiment, the method includes directing a calibration signal towards the detector such that at least a portion of the detector is exposed to the calibration signal in a substantially uniform manner for a predetermined acquisition time to generate a response signal.

In one embodiment, varying the intensity of the calibration signal includes providing a first and a second signal intensity. Varying the acquisition time includes providing a first and a second signal acquisition time thereby allowing determination of two to four components of a given response signal. In one embodiment, the first signal intensity includes a substantially uniform non-zero intensity and the second signal intensity includes a substantially nil intensity. In one embodiment, the first acquisition time includes a long signal acquisition time and the second acquisition time includes a short signal acquisition time. The long acquisition time is greater than the short acquisition time. In one embodiment, four components are resolved for a given response signal: (a) a first component that depends on both the calibration signal intensity and the acquisition time; (b) a second component that depends on the calibration signal intensity but not on the acquisition time; (c) a third component that depends on the acquisition time but not on the calibration signal intensity; and (d) a fourth component that depends neither on the calibration signal intensity or the acquisition time.

In one embodiment where such four components are resolved, first component includes a baseline component. The second component includes a contribution to the response signal when the calibration signal intensity transitions from the non-zero intensity to the substantially nil intensity. The third component includes a dark signal component. The fourth component includes a contribution to the response signal during an idle period following the acquisition time.

BRIEF DESCRIPTION OF THE DRAWINGS

FIG. 1A illustrates a functional block diagram of a system adapted to measure components associated with biological related processes;

FIG. 1B illustrates an example system adapted to perform a DNA fragment analysis;

FIG. 2 illustrates an error processing system configured to determine various components errors and/or calibration quantities associated with the measured signals;

DETAILED DESCRIPTION OF CERTAIN EMBODIMENTS

Figure 3:
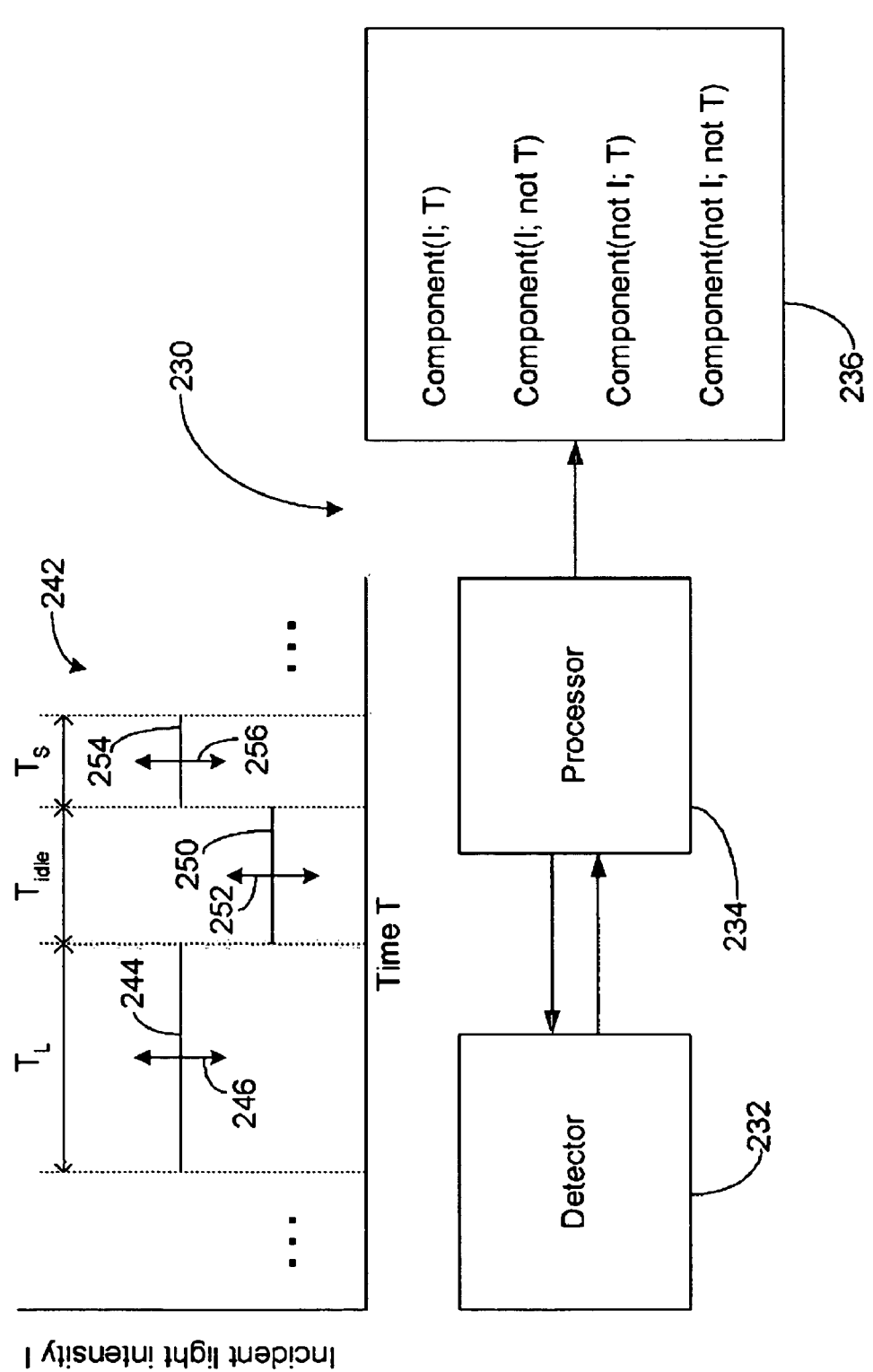
FIG. 3 illustrates a general methodology and result of a calibration method performed by the error processing system.

These and other aspects, advantages, and novel features of the present teachings will become apparent upon reading the following detailed description and upon reference to the accompanying drawings. In the drawings, similar elements have similar reference numerals.

FIG. 1A illustrates an example schematic diagram for a biological analyzer 90 capable of sequence determination or fragment analysis for nucleic acid samples. In various embodiments, the analyzer 90 may comprise one or more components or devices that are used for labeling and identification of the sample and may provide means for performing automated sequence analysis. The various components of the analyzer 90, described in greater detail hereinbelow, may comprise separate components or a singular integrated system. The present teachings may be applied to both automatic and semi-automatic sequence analysis systems as well as to methodologies wherein some of the sequence analysis operations are manually performed. Additionally, the methods described herein may be applied to other biological analysis platforms to improve the overall quality of the analysis In various embodiments, the methods and systems of the present teachings may be applied to numerous different types and classes of photo and signal detection methodologies and are not necessarily limited to CCD based detectors. Additionally, although the present teachings are described in various embodiments in the context of sequence analysis, these methods may be readily adapted to other devices/instrumentation and used for purposes other than biological analysis. For example, the present teachings may be applied to electronic telescopes and microscopes that utilize photo-detecting devices such as CCDs to improve the manner in which measured signals are identified and evaluated.

It will also be appreciated that the methods and systems of the present teachings may be applied to photo-detectors in general for a variety of applications, some of which are listed as examples above. Photo-detectors in general convert incident photons to electrical signals, and may include, by way example, CCDs, photomultipliers, or semiconductor based devices such as photo-diodes.

In the context of sequence analysis, the example sequence analyzer 90 may comprise a reaction component 92 wherein amplification or reaction sequencing (for example, through label incorporation by polymerase chain reaction) of various constituent molecules contained in the sample is performed. Using these amplification techniques, a label or tag, such as a fluorescent or radioactive dideoxy-nucleotide may be introduced into the sample constituents resulting in the production of a collection of nucleotide fragments of varying sequence lengths. Additionally, one or more labels or tags may be used during the amplification step to generate distinguishable fragment populations for each base/nucleotide to be subsequently identified. Following amplification, the labeled fragments may then be subjected to a separation operation using a separation component 94. In one aspect, the separation component 94 comprises a gel-based or capillary electrophoresis apparatus which resolves the fragments into discrete populations. Using this approach, electrical signal may be passed through the labeled sample fragments which have been loaded into a separation matrix (e.g. polyacrylamide or agarose gel). The application of an electrical signal results in the migration of the sample through the matrix. As the sample migration progresses, the labeled fragments are separated and passed through a detector 96 wherein resolution of the labeled fragments is performed.

In one aspect, the detector 96 may identify various sizes or differential compositions for the fragments based on the presence of the incorporated label or tag. In one example embodiment, fragment detection may be performed by generation of a detectable signal produced by a fluorescent label that is excited by a laser tuned to the label's absorption wavelength. Energy absorbed by the label results in a fluorescence emission that corresponds to a signal measured for each fragment. By keeping track of the order of fluorescent signal appearance along with the type of label incorporated into the fragment, the sequence of the sample can be discerned. A more detailed explanation of the sequencing process is provided in commonly assigned U.S. Pat. No. 6,040,586, entitled "Method and System for Velocity-Normalized Position-Based Scanning" which is hereby incorporated by reference in its entirety.

FIG. 1B, further illustrates example components for the detector 96 which may be used to acquire the signal associated with a plurality of labeled fragments 100. As previously indicated, the labeled fragments 100 may be resolved by measuring the quantity of fluorescence or emitted energy generated when the fragments 100 are subjected to an excitation source 114 of the appropriate wavelength and energy (e.g. a tuned laser). The energy emissions 120 produced by a label 116 associated with the fragments 100 may be detected using a charge-coupled device (CCD) 122 as the fragments 100 pass across a detection window 123 wherein a plurality of energy detecting elements (e.g., pixels) 124 capture at least a portion of the emitted energy from the label 116. In one aspect, an electronic signal 125 is generated by the CCD 122 that is approximately proportional to the relative abundance of the fragments 100 passing through the detection window 123 at the time of energy capture and the order which the fragments 100 appear in the detection window 123 may be indicative of their relative length with respect to one another.

A signal processor 126 is further configured to perform signal sampling operations to acquire the electronic signal generated by the CCD 122 in response to the fragments 100. In various embodiments, the signal processor 126 is configured to perform these sampling operations in a predetermined manner by signal acquisition over selected intervals. One aspect of the present teachings relates to the signal processor 126 being configured to allow determination of various signal components by utilizing the predetermined sampling patterns over the selected intervals.

In various embodiments, some of the information that may be determined through signal resolution and peak identification may include determination of the relative abundance or quantity of each fragment population. Evaluation of the signals may further be used to determine the sequence or composition of the sample using various known base sequence resolution techniques. It will further be appreciated by one of skill in the art that the exemplified signal distribution may represent one or more nucleic acid fragments for which the relative abundance of each fragment may be evaluated based, in part, upon the determination of the relative area of an associated peak in the signal distribution. The present teachings may therefore be integrated into existing analysis approaches to facilitate peak evaluation and subsequent integration operations typically associated with sequence analysis.

In various embodiments, the analysis of the signal 125 representative of the aforementioned example data may be advantageously performed by the signal processor 126. The signal processor 126 may further be configured to operate in conjunction with one or more processors. The signal processor's components may include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables. Furthermore, the signal processor 126 may output a processed signal or analysis results to other devices or instrumentation where further processing may take place.

In one aspect, the detector 96 may comprise a calibration energy source 630 that emits energy 632 directed at the detecting elements 124 for calibration processes described below in greater detail. The energy 632 may have a generally uniform and constant intensity to allow determination of the detecting elements' response to a known-intensity energy. In certain embodiment, the energy 632 comprises a visible light. It will be appreciated, however, that electromagnetic energy outside of the visible spectrum may be utilized for the concepts described herein without departing from the spirit of the present teachings.

In various embodiments, an objective of the present teachings is to improve the quality of the processed signals through various detector and signal related corrections. In certain embodiments, the CCD or another type of segmented detector and/or signal processor may be configured to provide normalization of the responses for the plurality of pixels. Such process is sometimes referred to as flat-fielding. A flat-fielding process 200 is depicted in FIG. 2, where a measured signal 202 is shown to comprise an actual signal 214 combined with a response component 216 (hashed) and a dark signal component 220 (shaded). The response component 216 and the dark signal component 220 are, for the purpose of this description, referred to as collectively referred to as an error component 222. Typically, each pixel corresponds a "channel," and channel-dependence of the actual signal 214 and the error component 222 are depicted as example five bins along the horizontal axis.

For the purpose of description, a signal and/or a signal component associated with various detectors and/or detector components can include, but not limited to, electrical charge and/or electrical current. For example, a signal from a given detector may include charge and/or current being read out from the detector.

A signal can also refer to an optical signal or other non-electrical signals. For example, a calibration signal can include, but not limited to, a light signal.

The actual signal 214 (and its channel distribution) depends on the physical processes being measured in the example measurement devices described above. The response component 216 may depend on each one or more operating parameters associated with each pixel. Such parameters may include, by way example, gain voltage of the channel and other readout related electronics noises associated with the channel. The dark signal component 220 may also be channel dependent, and generally comprises signals that result from the pixel without being induced by light. Such an effect may be a result of, by way of example, thermally induced signal. In certain applications, the dark signal component may be lumped into the channel dependent response component; hence, a single error component may represent a collection of substantially all the channel dependent noises.

Although the measured signal 202 in FIG. 2 is depicted as being comprised of the actual signal 214 and the error component 222, one generally does not know of such delineation unless the measured signal 202 is processed further. Typically, the objective of the further processing is to extract the actual signal 214 from the measured signal 202 by removing the error component 222. Thus in the example flat-fielding process 200, a dark signal signal 204 comprising the dark signal component 220 may be obtained and subtracted to yield a dark signal subtracted signal 206. One way to obtain the dark signal signal 204 is to provide a dark environment for the detector and operate the detector in a substantially same manner as that for obtaining the measured signal.

The dark signal subtracted signal 206 may still include the response component 216 that may cause the various channels to respond in a different manner. For example, if the detector is subjected to a substantially uniform intensity light, one would want to obtain a uniform response from each of the channels. In many applications, however, the different channels may output different signal values for a uniform input of light. As previously described, such non-uniformity may arise because of, for example, different gains in the different pixels.

One way to ascertain such non-uniformity in channel response is to operate the detector with a substantially uniform input light (e.g., a "flat-field" light). A measured flat-field signal 210 thus obtained preferably has its dark signal component subtracted in a manner similar to that described above. The dark signal subtracted signal 206 can then be divided by a properly scaled measured flat-field signal 210 to normalize the output of the channels so as to yield a processed signal 212 representative of the actual signal 214.

Traditionally, the dark signal component 220, response component 216, and any other components that contribute to the error component 222 are determined and compensated for in order to obtain the actual signal 214. One aspect of the present teachings relates to an error processing system 230 that analyzes the error component of the measured signal so as to identify and characterize various components of the error component in terms of different operating parameters associated with the detector. When implemented with the example flat-fielding process 200 described above, the error component 222 may be resolved into various subcomponents, wherein the subcomponents may be characterized in terms of some operating parameter of the CCD. It will be appreciated that the error processing method and system described herein may be utilized in conjunction with the flat-fielding process, or may be implemented by itself, or with any other signal quality enhancing process(es).

As illustrated in FIG. 3, certain embodiments of the error processing system 230 comprise an existing detector 232 (also depicted as 96 in FIG. 1A, 122 in FIG. 1B) and a processor 234 (also depicted as 126 in FIG. 1B) configured in a selected manner. In one possible configuration, the processor's existing firmware or drivers are modified in a manner so as to provide an ability to enable and disable a camera shutter while collecting signals during a specified period of time (referred to as "frame"), thus providing the ability to perform variable integration time frame measurements.

One aspect of the present teachings relates to manipulating the intensity of the light impinging on the detector, and the manner in which the signals from the controlled light are processed. Such methodology is depicted as an incident light intensity I profile 242 as a function of time T. The incident light may be obtained from the flat-field light source described above. Such light source may yield a substantially uniform intensity, depicted as substantially uniform values 244 during time period $T_L$, 250 during time period $T_{idle}$, and 254 during time period $T_S$. In one implementation, the period $T_L$ represents a "long" integration time frame, and the period $T_S$ represents a "short" integration time frame. Such long-short frames combination provides time variation, thereby allowing determination of time dependence of the various components of the measured signal. The substantially uniform value 244 of the incident light intensity may be varied, as depicted by an arrow 246. Such variation in the incident light intensity for a given time frame ($T_L$) allows determination of incident light intensity dependence of the various components of the measured signal. Similar variations in the incident light intensity may be performed with the substantially uniform values 250 and 254 during the periods $T_{idle}$ and $T_S$, respectively, as depicted by arrows 252 and 256.

The general concept of selectively varying the two parameters—incident light intensity (I) and time (T)—allows the processor 234 to determine various components of a given signal into four possible types of dependency combinations. As depicted in FIG. 3, an output 236 from the processor 234 may comprise the four types of components: a first component that depends on both I and T, a second component that depends on I but not T, a third component that depends on T but not I, and a fourth component that is independent of both I and T.

The long-short frame cycle depicted in FIG. 3 is particularly well suited for adaptation for I and T dependency determination in detector systems that are already configured to measure data in some combination of long and short frames. Such configuration may be used to extend the dynamic range of a detector by scaling the signal from the short frame to what the long frame signal would have been had it been allowed to exceed the upper limit of the dynamic range. Such methodology and other concepts are disclosed in U.S. Pat. No. 6,894,264 issued May 17, 2005 and titled "SYSTEM AND METHODS FOR DYNAMIC RANGE EXTENSION USING VARIABLE LENGTH INTEGRATION TIME SAMPLING," which is hereby incorporated by reference in its entirety.

It will be appreciated that while the use of long-short frame combination is convenient in systems already configured to operate as such, that existing capability is not a requirement for implementation of the present teachings. A given system, without the existing long-short frame combination, may be adapted to perform such similar tasks without departing from the spirit of the present teachings.

Figure 4:
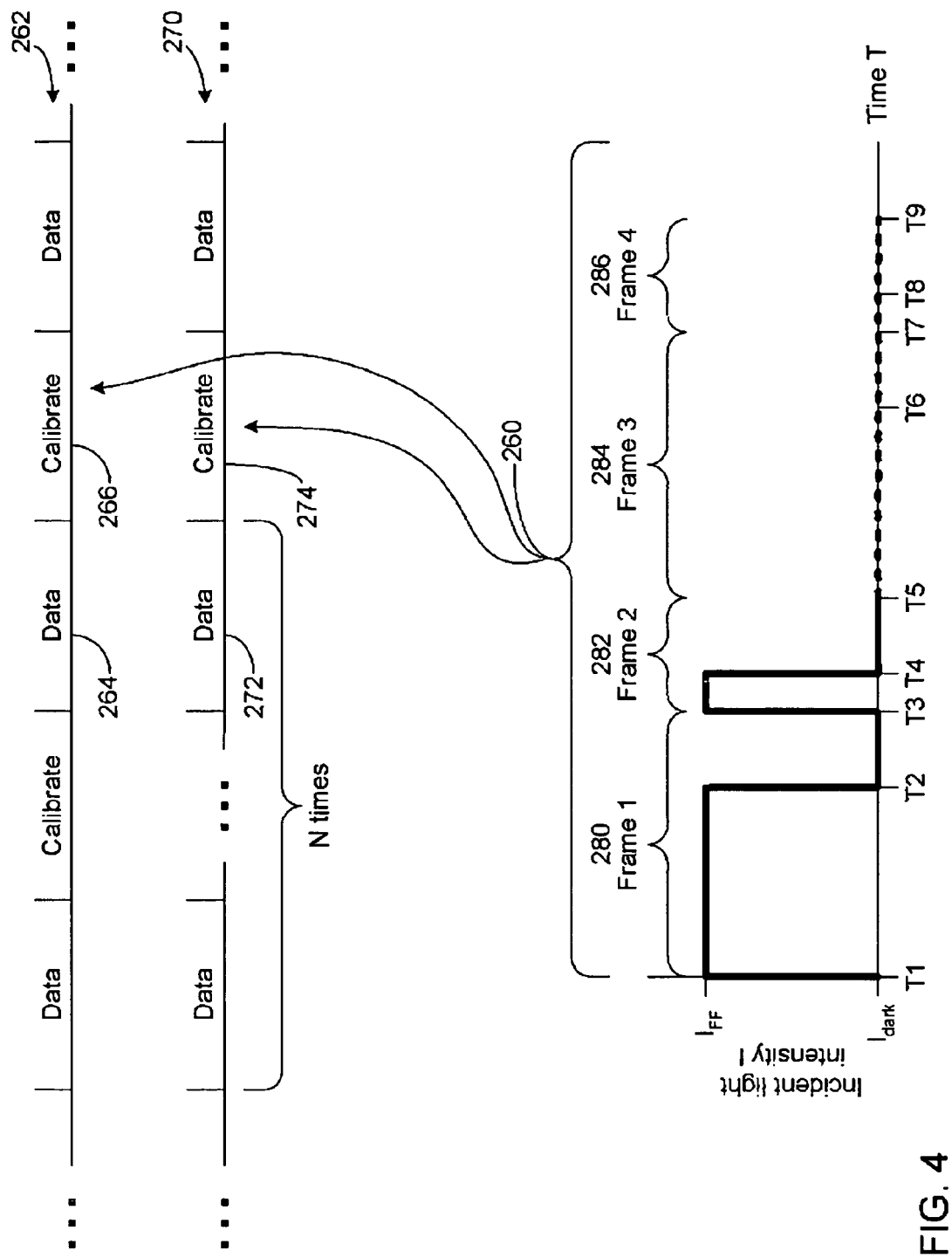
FIG. 4 illustrates the example calibration sequence configured to utilize and be part of an existing data collection sequence.

FIG. 4 illustrates one possible implementation of a calibration set 260 that includes variations in the incident light intensity and the integration time. The calibration set 260 comprises a series of four frames 280, 282, 284, and 286 (denoted as frames one to four) that may be obtained in any order. Certain orders, however, may be easier to implement due to various factors. For example, if a given system is configured to perform an alternating pattern of long-short-long-short- etc., it makes more sense to retain such pattern in the calibration set.

As seen in FIG. 4, the calibration set 260 comprises the incident light intensity I having either of two values—a flat-field light intensity $I_{FF}$ or a dark condition intensity $I_{dark}$. Such transition between the two intensities may be achieved by use of a shutter to either allow or prevent light from reaching the detector. Furthermore, each of the long and short frames are shown to include a period (T2–T3, T4–T5, T6–T7, and T8–T9) after their respective integration periods. Such a period is referred to as an idle period (or sometimes referred to as a "dead time") associated with time required to read out the pixel and reset the pixel for further detection. The aforementioned idle periods are depicted to have an approximately same duration, regardless of whether the frame is long or short. However, such a choice of the idle periods is not a requirement. In certain embodiments, the shutter is closed during the idle periods, such that the detector experiences the dark condition.

Thus, the first frame 280 of the example calibration set 260 comprises an integration of $I_{FF}$ intensity light during T1 to T2, followed by the idle period from T2 to T3. The second frame 282 comprises an integration of $I_{FF}$ intensity light during T3 to T4, followed by the idle period from T4 to T5. The third frame 284 comprises an integration of $I_{dark}$ intensity light (i.e., dark) during T5 to T6, followed by the idle period from T6 to T7. The fourth frame 286 comprises an integration of $I_{dark}$ intensity light (i.e., dark) during T7 to T8, followed by the idle period from T8 to T9.

Preferably, the first integration period T1 to T2 is substantially same as the third integration period T5 to T6, with the difference in the two periods being the incident light intensity of $I_{FF}$ versus $I_{dark}$. Similarly, the second integration period T3 to T4 is substantially same as the fourth integration period T7 to T8. The integrations of the long and short dark periods permit determination of any time dependence of a channel response in the absence of an incident light in a manner described below in greater detail. In FIG. 4, the first and second frames 280 and 282 are referred to as baseline frames for the purpose of this description (depicted as solid line), and may be achieved by opening the shutter during the periods of T1 to T2 and T3 to T4 and keeping the shutter closed at other times. The third and fourth frames 284 and 286 are referred to as dark frames for the purpose of this description (depicted as dashed line), and may be achieved by keeping the shutter closed during the time from T5 to T9.

As further illustrated in FIG. 4, the calibration set 260 achieved in the foregoing manner may be incorporated into a variety of data collection sequences, such as two example sequences 262 and 270. In the example sequence 262, the calibration set 260 is performed during calibration blocks 266 temporally disposed between data blocks 264. In the example sequence 270, the calibration set 260 is performed during a calibration block 274 after every N data blocks 274. It should be apparent that any other combination of the data and calibration blocks may be implemented into a sequence without departing from the spirit of the present teachings. Preferably, the calibration to determine the various error and response components are determined under a condition as close to the data condition as possible.

During the data blocks, the light to the detector is provided via the sample being measured, whereas during the calibration blocks, the baseline light and the dark condition is provided by a combination of the flat-field light source and the shutter. Thus, the frequency of the calibration data blocks in a given sequence may be determined by factors such as how easily the light sources can be switched (between the sample and the baseline light/dark condition), the extent of "down time" during switching of samples, and the stability of the system. For example, if the down time between samples is larger than the calibration block time scale, calibration may be performed between each data block regardless of whether it is needed or not. In another example, if the sample comprises multiple cells arranged in an array, and the cell-to-cell movement can be achieved substantially faster than the calibration time scale, one may want to tailor the calibration scheme based on the stability of the system.

Figure 5:
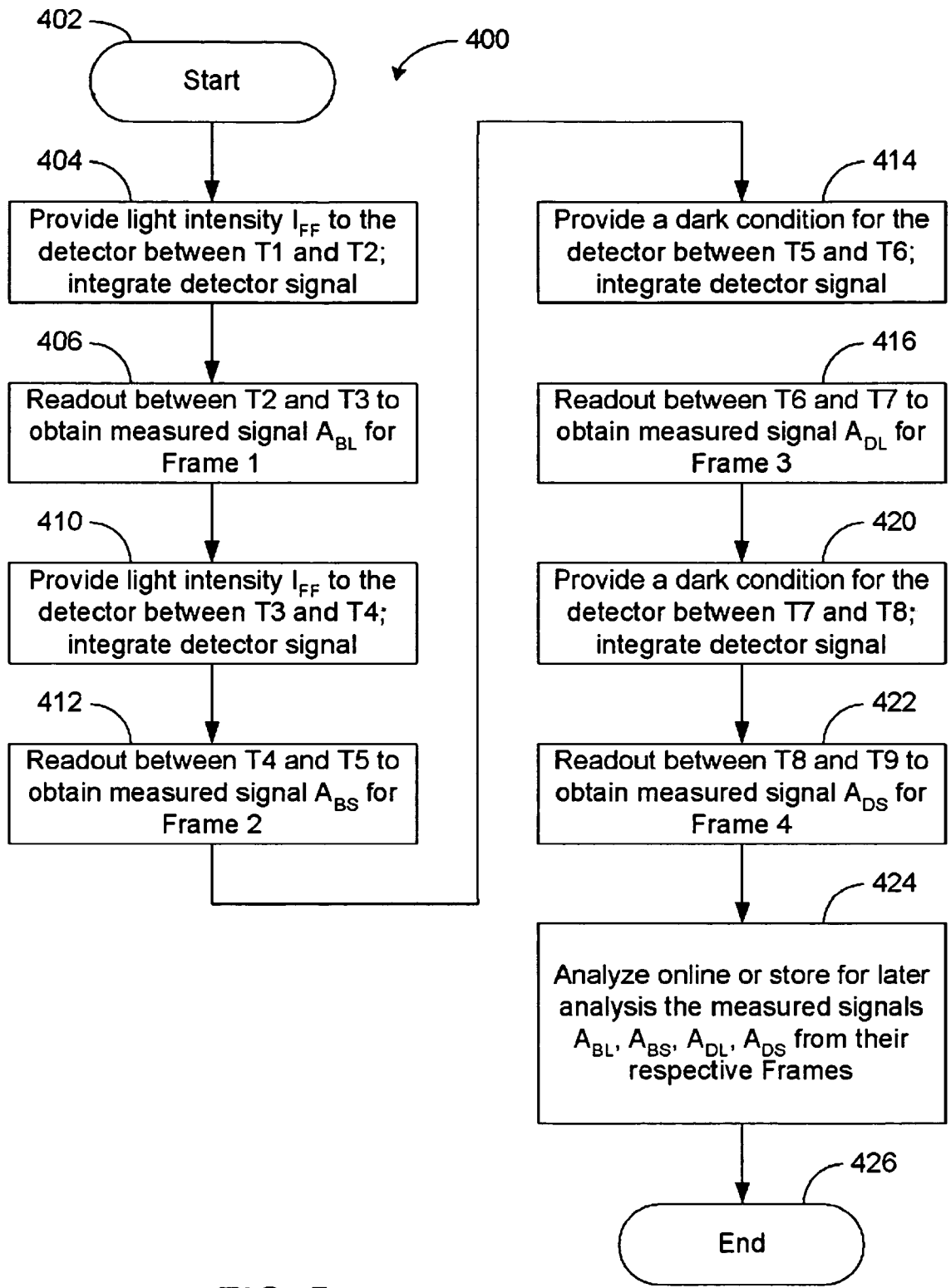
FIG. 5 illustrates an example process for performing the example calibration sequence of FIG. 4 and processing the measured signals therefrom.

FIG. 5 now illustrates a process 400 that determines various measured signals during the calibration set 260 described above in reference to FIG. 4. Thus, the process 400 preferably occurs in each of the calibration blocks also described above in reference to FIG. 4. The process 400 may be performed by the processor 300 in conjunction with the detector 232 described above in reference to FIG. 3.

The process 400 begins at a start state 402, and in state 404 that follows, the baseline flat-field light with intensity $I_{FF}$ is provided to the detector during the period T1 to T2, and the resulting signal from the detector is integrated. In state 406 that follows, the process 400 reads out the total measured signal $A_{BL}$ for the first frame during the idle period T2 to T3. The "BL" subscript denotes "baseline-long," meaning that the baseline light with intensity $I_{FF}$ is integrated for the long period. In state 410 that follows, the baseline flat-field light with intensity $I_{FF}$ is provided to the detector during the period T3 to T4, and the resulting signal from the detector is integrated. In state 412 that follows, the process 400 reads out the total measured signal $A_{BS}$ for the second frame during the idle period T4 to T5. The "BS" subscript denotes "baseline-short," meaning that the baseline light with intensity $I_{FF}$ is integrated for the short period.

In state 414 that follows, the dark condition is provided for the detector during the period T5 to T6, and the resulting signal from the detector is integrated. In state 416 that follows, the process 400 reads out the total measured signal $A_{DL}$ for the third frame during the idle period T6 to T7. The "DL" subscript denotes "dark-long," meaning that dark signal is integrated for the long period. In state 420 that follows, the dark condition is provided for the detector during the period T7 to T8, and the resulting signal from the detector is integrated. In state 422 that follows, the process 400 reads out the total measured signal $A_{DS}$ for the fourth frame during the idle period T8 to T9. The "DS" subscript denotes "dark-short," meaning that dark signal is integrated for the short period.

In state 424 that follows, the measured signals $A_{BL}$, $A_{BS}$, $A_{DL}$, and $A_{DS}$ corresponding to the first to fourth frames may be analyzed online to determine the various error and response components. Such results can be applied to the applicable data blocks online to enhance the quality of the data. Alternatively, the measured signals $A_{BL}$, $A_{BS}$, $A_{DL}$, and $A_{DS}$ may be stored for later analysis to determine the various error and response components so as to enhance the data quality. The process 400 stops at end state 426.

For the purpose of description herein, the example calibration set 260 is described as including the frames BL, BS, DL, and DS. It will be understood that the calibration set can include these for frames in any order. Further more, the four frames can be separated into different calibration sets. For example, BL and BS can form one calibration set, and DL and DS can form another calibration set. These two example calibration sets can be performed at different times—for example, in an alternating manner. It will also be understood that any other combinations of the frames can be used to form the example calibration sets each having two frames. Within each of the two-frame calibration sets, the two frames can, of course, be arranged in any of the possible combinations. In general, it will be understood that the calibration set(s) can be formed and performed in any of the possible combinations of the individual frames.

It will also be understood that in some embodiments, calibration sets having any of the foregoing combinations of BL, BS, DL, and DS frames can include average frames obtained by averaging of multiple frames. For example, an average BL frame can be obtained by averaging of multiple BL frames.

Figure 6:
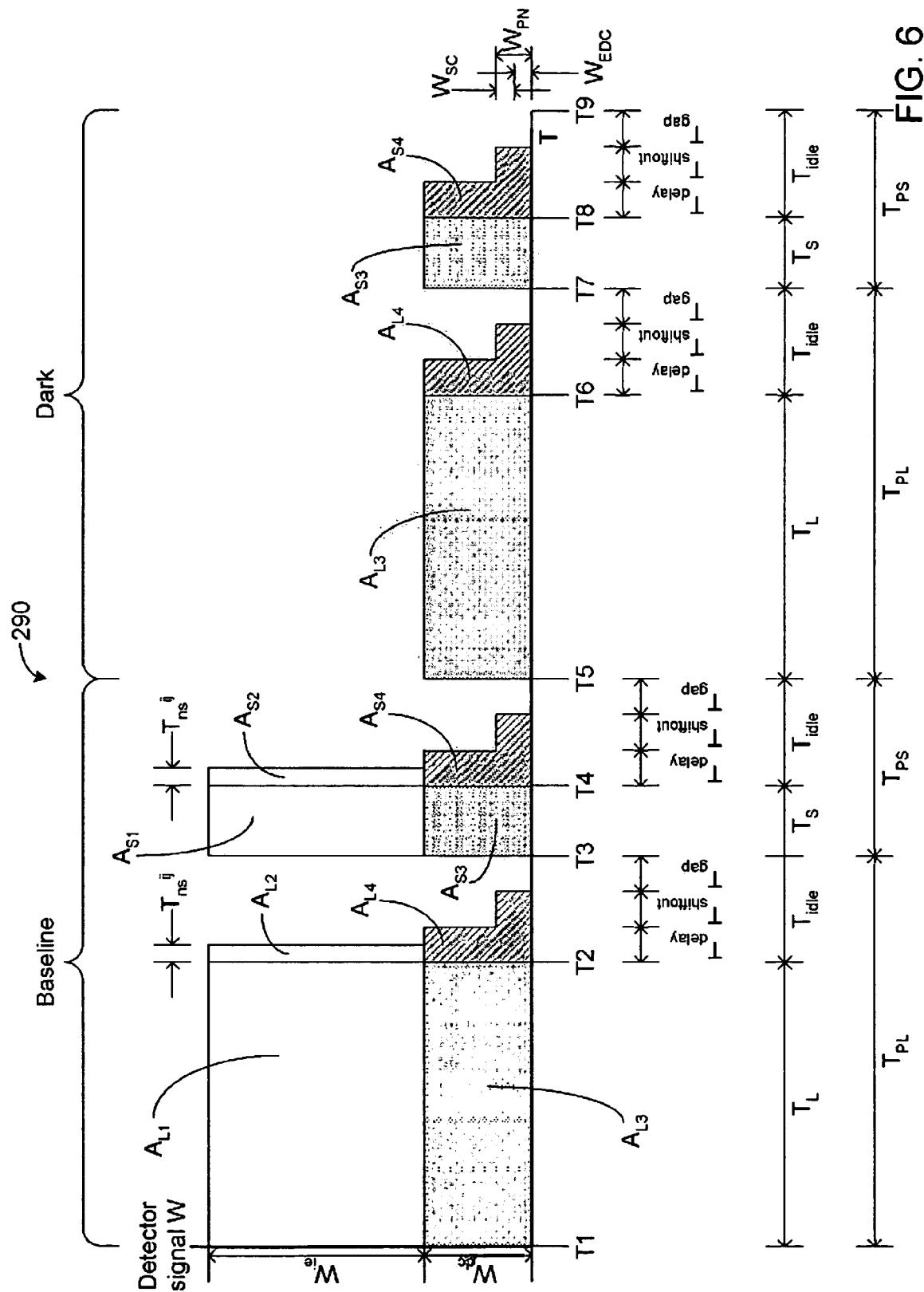
FIG. 6 illustrates an example structure of the measured signals from the example calibration sequence of FIG. 4.

FIGS. 3–5 describe the calibration performed by the processor (in conjunction with the detector) in terms of operational parameters I (incident light intensity) and time T to obtain the measured signal values $A_{BL}$, $A_{BS}$, $A_{DL}$, and $A_{DS}$. In particular, the calibration process 400 performed in the foregoing manner yields the measured signal values $A_{BL}$, $A_{BS}$, $A_{DL}$, and $A_{DS}$. FIG. 6 now depicts how such measured signal values may be represented in terms of a detector signal W and time T. The detector signal W is due to the incident light impinging on the detector, and also due to the manner in which the detector is being operated. For example, dark signal results from the CCD even in the absence of incident light, and the amount of such signal depends on operating parameters such as temperature.

It should be understood that while FIG. 6 illustrates the signal profiles of the four frames as being composites of different components, such depiction is for descriptive purpose only. At the time of the measurement, one does not know the values of the different components. Instead, only the four measured signal values $A_{BL}$, $A_{BS}$, $A_{DL}$, $A_{DS}$, along with certain substantially fixed time parameters are available. Further processing of these quantities, in a manner described below, allow determination of the different components depicted in FIG. 6, thereby allowing improved characterization of the performance of the detector and its associated readout chain.

A detector signal output profile 290 corresponds to the four frames described above in reference FIGS. 4 and 5. The first and second frames are categorized as baseline frames, and the third and fourth frames are categorized as dark frames. As before, the first frame begins at T1 and ends at T3, and the total duration is assigned a value of $T_{PL}$. The $T_{PL}$ time period is a sum of the long integration time $T_L$ and the idle time $T_{idle}$ such that $T_{PL}=T_L+T_{idle}$. Ideally, the long integration time $T_L$ ends at time T2; however, there may exist an integration time nonuniformity $T_{ns}^{ij}$ (superscript indices ij referring to pixel indices ij) that results from effects such as slow shutter and the pixel's response to the integration halt. As a consequence, there may be a residual signal from the detector beyond time T2 when the shutter-close command is issued. Thus, although the long integration time $T_L$ is depicted as terminating at T2, it may end slight prior to or after T2 (by approximately $T_{ns}^{ij}$); thus $T_L$ is not a substantially constant value on which other quantities may be based on. The total time $T_{PL}$, however, may be selected to be a substantially fixed quantity for such purpose.

Similarly, the beginning of idle time $T_{idle}$, nominally at T2, floats with the actual end of $T_L$. The idle time $T_{idle}$ may be broken down into a sequence of $T_{delay}$, $T_{shiftout}$, and $T_{gap}$. The time $T_{delay}$ represents a delay between the shutter close command at T2 and the time at which accumulated charges in the pixels are shifted out (read out). Such shiftout lasts for $T_{shiftout}$, and may be followed by a gap of time $T_{gap}$ before the start of the next frame. During the idle time $T_{idle}$, additional non-light related signal may be associated with a given pixel and its associated readout chain, thereby adding to the overall readout charge.

The second, third, and fourth frames also have similar time structures as that of the first frame described above. Specifically, the short frames, the second and fourth frames, can each be defined by a substantially fixed total time $T_{PS}$. The long frames, the first and third frames, can be defined by the substantially fixed total time $T_{PL}$.

The four frames defined time-wise in the foregoing manner yield the measured signal values $A_{BL}$, $A_{BS}$, $A_{DL}$, and $A_{DS}$. Each of these measured values may be broken down into four components as $$A_{measured} = A_{light} + A_{ns} + A_{dark} + A_{idle} \qquad (1)$$

where $A_{measured}$ can be any one of $A_{BL}$, $A_{BS}$, $A_{DL}$, $A_{DS}$. $A_{light}$ represents a signal resulting from the incident light, and in FIG. 6 is denoted as $A_{L1}$ and $A_{S1}$, where the subscript denotes long or short. $A_{light}=0$ for the dark third and fourth frames. $A_{ns}$ represents a signal resulting from the integration time nonuniformity $T_{ns}^{ij}$ with the incident light, and in FIG. 6 is denoted as $A_{L2}$ and $A_{S2}$, where the subscript denotes long or short. $A_{ns}=0$ for the dark third and fourth frames. $A_{dark}$ represents a dark signal that results during the integrations, and such signal is present whether or not the detector is subjected to light. In FIG. 6, $A_{dark}$ is denoted as $A_{L3}$ for the long frames and $A_{S3}$ for the short frames. $A_{idle}$ represents a collective signal resulting during the idle time, and in FIG. 6 is denoted as $A_{L4}$ for the long frames and $A_{S4}$ for the short frames.

As illustrated in FIG. 6, the dark signal components $A_{L3}$ and $A_{S3}$ have an effective dark signal magnitude $W_{dc}$, and the signal components associated with light ($A_{L1}$, $A_{L2}$, $A_{S1}$, $A_{S2}$) have an effective light-based signal magnitude $W_{ie}$. It should be understood that the signal magnitude $W_{ie}$ may be related to the incident light intensity by some conversion factor that accounts for light-photoelectron conversion effects such as quantum efficiency of the pixel. Thus, for the flat-field light source, the signal magnitude $W_{ie}$ may be considered to be proportional to the substantially constant light intensity I described above.

As previously described, the measured signals $A_{BL}$, $A_{BS}$, $A_{DL}$, and $A_{DS}$ during the four frames do not yield the signal and time breakdown as described in reference to FIG. 6. One aspect of the present teachings relates to analyzing the measured $A_{BL}$, $A_{BS}$, $A_{DL}$, $A_{DS}$, the frame durations $T_{PL}$, $T_{PS}$ in context of the components model exemplified in FIG. 6.

Figure 7:
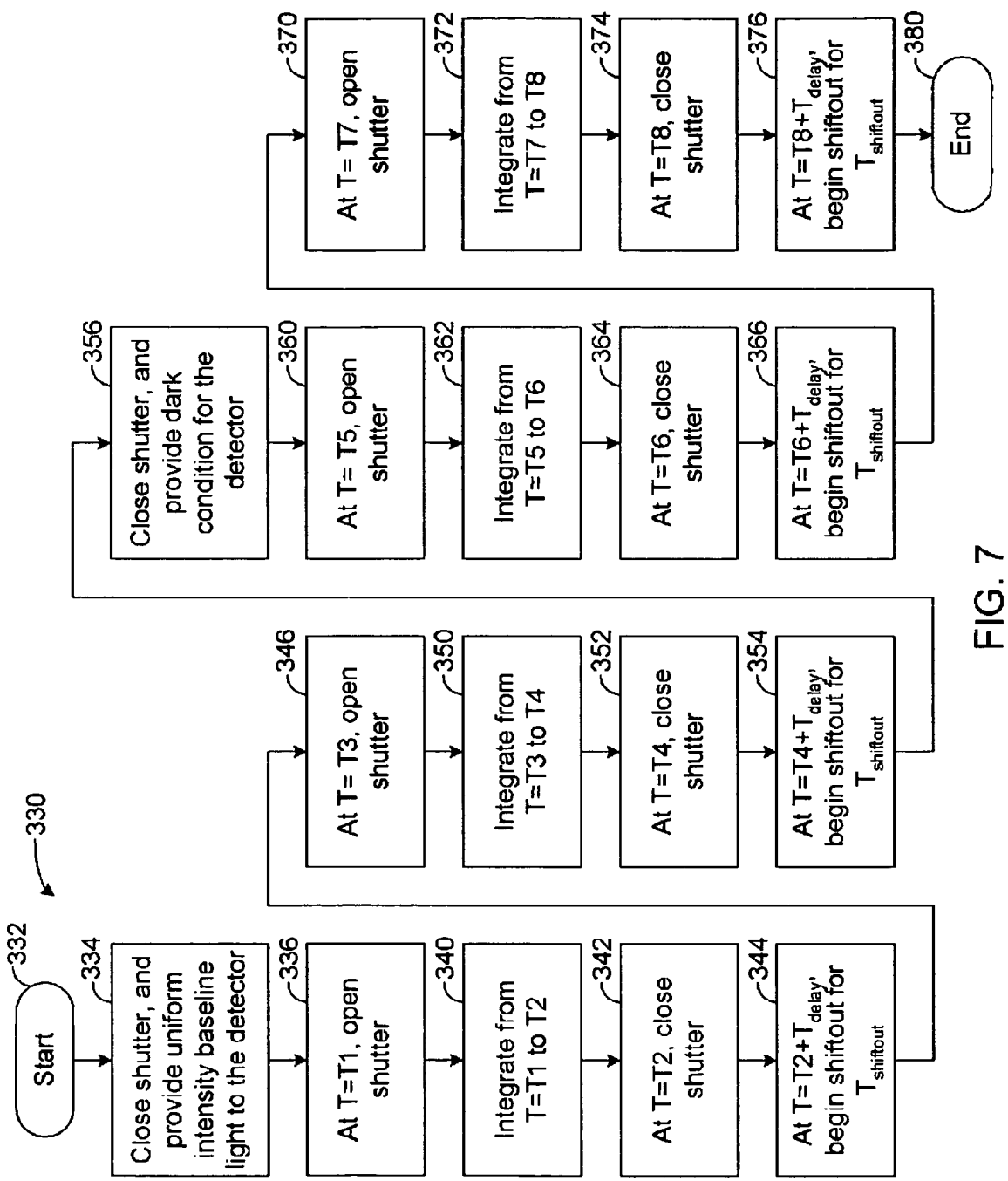
FIG. 7 illustrates an example process that can yield the example signal structure of FIG. 6.

Prior to description of such analysis, FIG. 7 illustrates a process 330 that yields the detector signal output profile 290 of FIG. 6. The process 330 begins at start state 332, and in state 334 that follows, the shutter is closed and uniform intensity baseline light is provided for the detector. In state 336 that follows, shutter is opened at time T1. The steps of turning on the light first and opening the shutter at time T1 assumes that the shutter response is faster and controllable than turning on of the light source to a uniform intensity level. But such an assumption is in no way intended to limit the scope of the process 330. Any baseline light/shutter operation combination may be implemented in the process 330 without departing from the spirit of the present teachings. For example, the baseline light may remain on constantly, and the light/dark condition of the detector may be determined by the shutter operation.

In state 340, the process 330 perform the long integration with light from T1 to T2. In state 342 that follows, the shutter is closed. In state 344 that follows, the process 330 delays for $T_{delay}$ and performs the shiftout for $T_{shiftout}$, possibly followed by a gap time of $T_{gap}$ so as to complete the first frame.

In state 346, the shutter is opened at time T3. In state 350 that follows, the process 330 performs the short integration with light from T3 to T4. In state 352 that follows, the shutter is closed. In state 354 that follows, the process 330 delays for $T_{delay}$ and performs the shiftout for $T_{shiftout}$, possibly followed by a gap time of $T_{gap}$ so as to complete the second frame.

In state 356, the shutter is closed and dark condition is provided for the detector. As previously described, the dark condition may be provided by the closed shutter itself. Alternatively, the baseline light may be turned off for the remainder of the process 330. For the purpose of description of the process 330, and for consistency in the shutter open/close sequence in the other frames, the baseline light will be assumed to be turned off during the performance of the third and fourth frames. In state 360, the shutter is opened at time T5. In state 362 that follows, the process 330 performs the long integration without light from T5 to T6. In state 364 that follows, the shutter is closed. In state 366 that follows, the process 330 delays for $T_{delay}$ and performs the shiftout for $T_{shiftout}$, possibly followed by a gap time of $T_{gap}$ so as to complete the third frame.

In state 370, the shutter is opened at time T7. In state 372 that follows, the process 330 performs the short integration without light from T7 to T8. In state 374 that follows, the shutter is closed. In state 376 that follows, the process 330 delays for $T_{delay}$ and performs the shiftout for $T_{shiftout}$, possibly followed by a gap time of $T_{gap}$ so as to complete the fourth frame. The process 330 stops at end state 380.

The process 330 performed in the foregoing manner yields the measured signals $A_{BL}$, $A_{BS}$, $A_{DL}$, and $A_{DS}$ during the four frames specified by the frame durations $T_{PL}$, $T_{PS}$. One aspect of the present teachings relates to determination of the four components of each of the four frames described above in reference to FIG. 6. Specifically, applying Equation 1 to each of the four frames, the measured signals corresponding to the four frames can be expressed fully as $$A_{BL} = A_{BL1} + A_{BL2} + A_{BL3} + A_{BL4} \qquad (2a)$$

$$A_{BS} = A_{BS1} + A_{BS2} + A_{BS3} + A_{BS4} \qquad (2b)$$

$$A_{DL} = A_{DL1} + A_{DL2} + A_{DL3} + A_{DL4} \qquad (2c)$$

$$A_{DS} = A_{DS1} + A_{DS2} + A_{DS3} + A_{DS4} \qquad (2d)$$

where the subscripts "B" and "D" have been added to distinguish between the baseline and dark frames. In context of the example model of the detector signal output profile 290 of FIG. 6, however, the such subscripts can be dropped (and is dropped in FIG. 6). In particular, $A_{DL1} = A_{DS1} = 0$ since no light impinges on the detector during the dark frames. Similarly, $A_{DL2} = A_{DS2} = 0$. Thus, there is no need to keep the "B" subscript in $A_{BL1}$, $A_{BS1}$, $A_{BL2}$, and $A_{BS2}$, and can be expressed as $A_{L1}$, $A_{S1}$, $A_{L2}$, and $A_{S2}$, as done in FIG. 6 and its related description herein. In a similar manner, the "B" and "D" subscripts can be dropped from the dark signal components $A_{BL3}$, $A_{BS3}$, $A_{DL3}$, and $A_{DS3}$ (and be expressed as $A_{L3}$ and $A_{S3}$ for both baseline and dark frames) because the dark signal component is present during integrations and is generally independent of the incident light intensity. In a similar manner, the "B" and "D" subscripts can be dropped from the idle signal components $A_{BL4}$, $A_{BS4}$, $A_{DL4}$, and $A_{DS4}$ (and be expressed as $A_{L4}$ and $A_{S4}$ for both baseline and dark frames) because the idle signal component is generally independent of the incident light intensity. For the foregoing reasons, Equations 2a–d can be expressed as $$A_{BL} = A_{L1} + A_{L2} + A_{L3} + A_{L4} \quad (3a)$$

$$A_{BS} = A_{S1} + A_{S2} + A_{S3} + A_{S4} \quad (3b)$$

$$A_{DL} = A_{L3} + A_{L4} \quad (3c)$$

$$A_{DS} = A_{S3} + A_{S4}. \quad (3d)$$

Referring to FIG. 6, the eight components on the right sides of the Equations 3a–d, namely $A_{L1}$, $A_{L2}$, $A_{L3}$, $A_{L4}$, $A_{S1}$, $A_{S2}$, $A_{S3}$, $A_{S4}$ can be characterized as $$A_{L1} = W_{ie} T_L \quad (4a)$$

$$A_{L2} = W_{ie} T_{ns}^{ij} \quad (4b)$$

$$A_{L3} = W_{dc} T_L \quad (4c)$$

$$A_{L4} = A_{DL} - A_{L3} \quad (4d)$$

$$A_{S1} = W_{ie} T_S \quad (4e)$$

$$A_{S2} = W_{ie} T_{ns}^{ij} = A_{L2} = A_2 \quad (4f)$$

$$A_{S3} = W_{dc} T_S \quad (4g)$$

$$A_{S4} = A_{DS} - A_{S3}. \quad (4h)$$

The indices ij refer to pixel indices ij. Equation 4 h can be simplified further in calibration sets where the idle periods (and their temporal sub-structures) are substantially the same for the long and short frames, such that $A_{S4} = A_{L4} = A_4$. Although the simplification is not a requirement, such assumption is made in the subsequent analysis.

Figure 8:
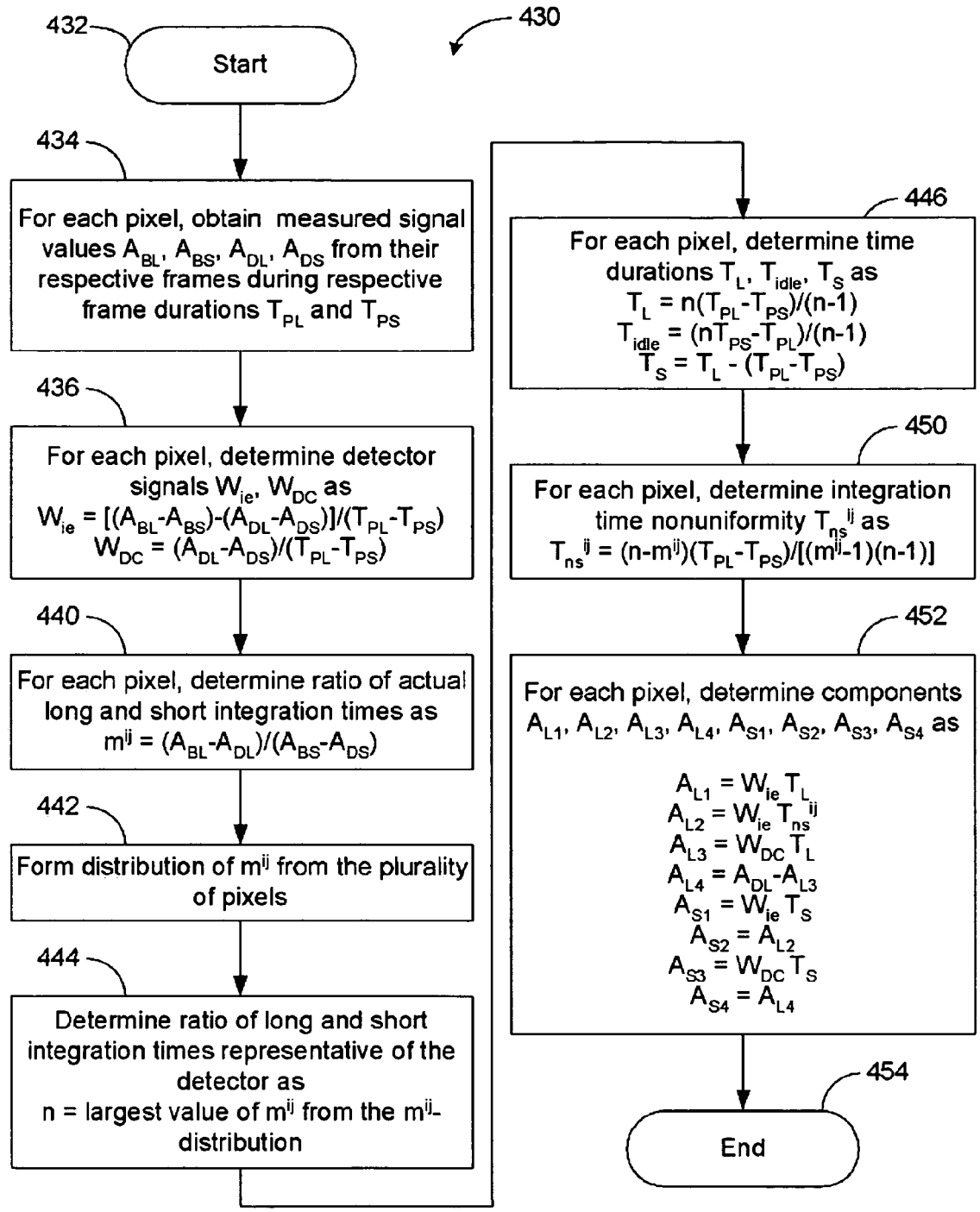
FIG. 8 illustrates an example process that can determine the quantities associated with the components of the example signal structure of FIG. 6.

FIG. 8 now illustrates one possible process 430 for determining the various parameters (on the right sides of Equations 4a–h) associated with the components of the four frames. It will be understood that given the knowns $A_{BL}$, $A_{BS}$, $A_{DL}$, $A_{DS}$, $T_{PL}$, $T_{PS}$, and the example model of the detector signal output profile 290 of FIG. 6, there are any number of different ways of algebraically manipulating the knowns to ultimately generate similar results that may be used in Equations 4a–h. As previously described, such determination (process 430) may be performed online as the calibration sets are obtained, or the measured values may be stored for later analysis.

In FIG. 8, a process 430 begins in a start state 432. In state 434 that follows, the process 430, for each of the plurality of pixels, obtains the measured signals $A_{BL}$, $A_{BS}$, $A_{DL}$, $A_{DS}$ from their respective frames during respective frame durations $T_{PL}$ and $T_{PS}$.

In state 436 that follows, the process 430 determines the detector signal magnitudes $W_{dc}$ and $W_{ie}$ for each pixel. The magnitude $W_{dc}$ can be determined by considering the dark long (third) and the dark short (fourth) frames of FIG. 6 and Equations 3c–d, and noting that the differences in the measured signal values $$A_{DL} - A_{DS} = (A_{L3} + A_{L4}) - (A_{S3} + A_{S4}) = A_{L3} - A_{S3} \quad (5)$$

since $A_{S4} = A_{L4} = A_4$. Furthermore, $A_{L3} = W_{dc} T_L$, and $A_{S3} = W_{dc} T_S$. Hence, Equation 5 can be rewritten as $$A_{DL} - A_{DS} = W_{dc} (T_L - T_S). \quad (6)$$

Since, the substantially fixed times $T_{PL}$ and $T_{PS}$ are respectively $T_L + T_{idle}$ and $T_S + T_{idle}$, with the integration-to-idle ($T_{L/S}$ to $T_{idle}$) transition sliding (by $T_{ns}^{ij}$) in the substantially same manner for both the long and short frames, the time difference $$T_L - T_S = T_{PL} - T_{PS}. \quad (7)$$

Hence, $W_{dc}$ from Equation 6 may be expressed in terms of measured or known quantities as $$W_{dc} = (A_{DL} - A_{DS})/(T_{PL} - T_{PS}). \quad (8)$$

In a similar manner (omitting some obvious or similar algebraic steps in the derivation of Equation 8), $$A_{BL} - A_{BS} = W_{ie}(T_{PL} - T_{PS}) + W_{dc}(T_{PL} - T_{PS}). \quad (9)$$

Isolating the $W_{ie}$ and substituting the expression for $W_{dc}$ from Equation 8, $W_{ie}$ can be expressed as $$W_{ie} = [(A_{BL} - A_{BS}) - (A_{DL} - A_{DS})]/(T_{PL} - T_{PS}). \quad (10)$$

In state 440 that follows, the process 430 determines, for each pixel, a ratio $m^{ij}$ of the actual long and short integration times as $$m^{ij} = (T_L + T_{ns}^{ij})/(T_S + T_{ns}^{ij}). \quad (11)$$

Because the quantities on the right side of Equation 11 are not determined at this point, it is desirable to convert them to the known or determined quantities. One way is to multiply top and bottom of right side of Equation 11 by $W_{ie}$ such that $$m^{ij} = (W_{ie} T_L + W_{ie} T_{ns}^{ij})/(W_{ie} T_S + W_{ie} T_{ns}^{ij}) = (A_{L1} + A_2)/(A_{S1} + A_2). \quad (12)$$

From FIG. 6, one can see that $A_{L1} + A_2$ is simply the difference between the measured signals $A_{BL}$ and $A_{DL}$. Similarly, $A_{S1} + A_2 = A_{BS} - A_{DS}$. Thus, the ratio $m^{ij}$ can be expressed in terms of the known measured quantities as $$m^{ij} = (A_{BL} - A_{DL})/(A_{BS} - A_{DS}). \quad (13)$$

The ratio $m^{ij}$ allows determination of some of the time parameters as described below.

In state 442 that follows, the process 430 forms a distribution of the $m^{ij}$ values from the plurality of pixels of the detector. Considering the definition of $m^{ij}$ in Equation 11, and given that $T_L > T_S$, a zero value for $T_{ns}^{ij}$ corresponds to the maximum value of m. Conversely, the largest value for $T_{ns}^{ij}$ corresponds to the minimum value of m. Thus, the worst case limit of the integration time nonuniformity $T_{ns}^{ij}$ for the detector can be associated with the smallest value of $m^{ij}$ among the plurality of pixels.

Figure 16:
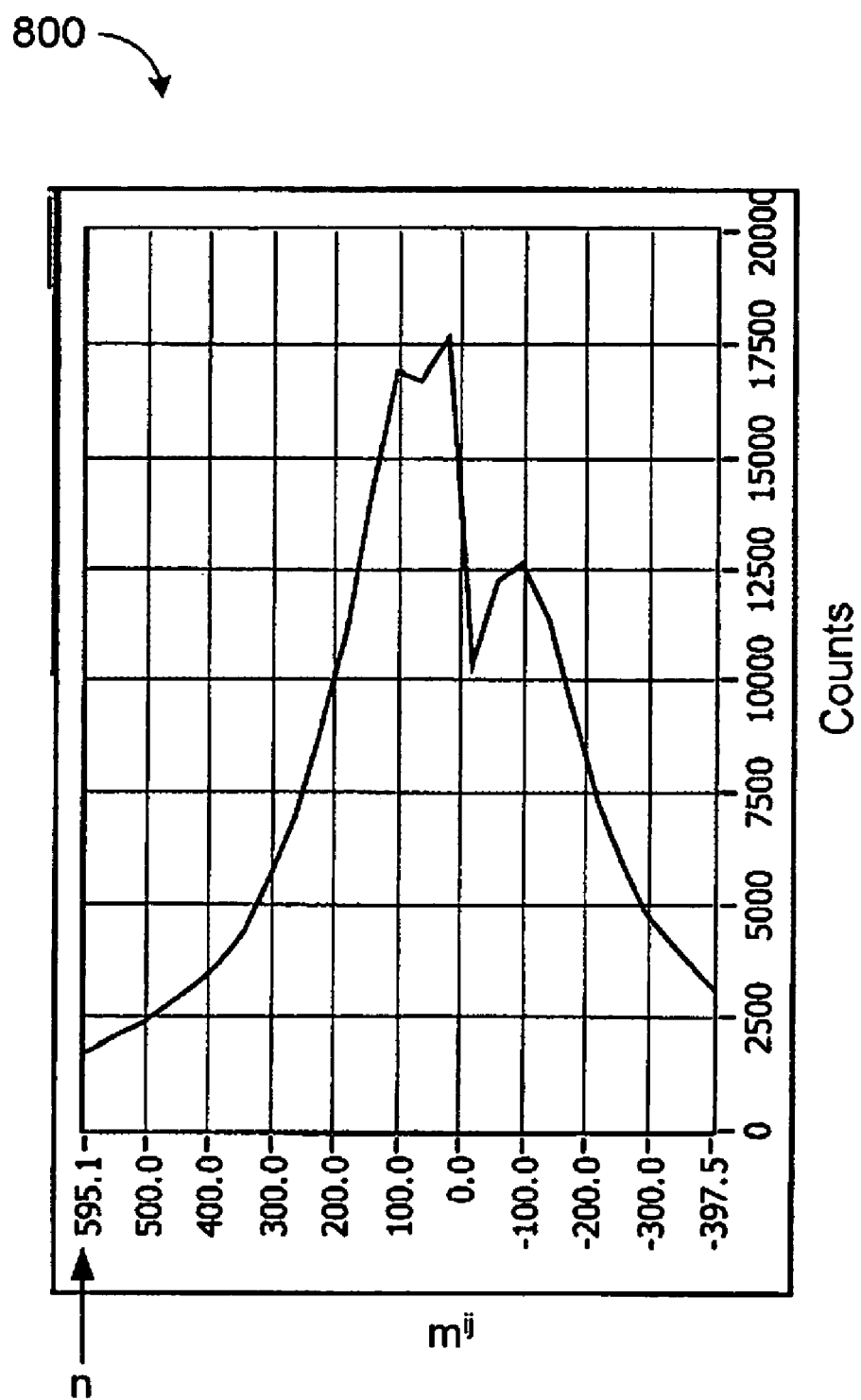
FIG. 16 illustrates an example distribution of a ratio $m^{ij}$ of actual long and short integration times corresponding to a plurality of pixels.

In state 444 that follows, the process 430 determines a ratio n of long and short integration times representative of the detector as the largest value of $m^{ij}$ from the $m^{ij}$ distribution. FIG. 16 shows an example $m^{ij}$ distribution 800 having a largest $m^{ij}$ value of approximately 595. Thus for the example $m^{ij}$ distribution 800, the value of n is approximately 595.

In state 446 that follows, the time durations $T_{idle}$, $T_L$, and $T_S$ are approximated for each pixel based in part on the detector-wide parameter n. For each pixel, the ratio n of long and short integration times may also be expressed as $$n = T_L/T_S = (T_{PL} - T_{idle})/(T_{PS} - T_{idle}). \quad (14)$$

Since the value of n is determined, and the long and short frame time intervals $T_{PL}$ and $T_{PS}$ are known values, $T_{idle}$ in Equation 14 may be solved to yield $$T_{idle} = (n T_{PS} - T_{PL})/(n - 1). \quad (15)$$

Now, since $T_L=T_{PL}-T_{idle}$, substituting the expression of $T_{idle}$ in Equation 15 yields an expression for $T_L$ as $$T_L=n(T_{PL}-T_{PS})/(n-1). \tag{16}$$

Furthermore, since $T_L-T_S=T_{PL}-T_{PS}$ (Equation 7), $T_S$ may be expressed as $$T_S=T_L-(T_{PL}-T_{PS}) \tag{17}$$

where $T_L$ is expressed in Equation 16.

In state 450 that follows, the process 430 determines the integration time nonuniformity $T_{ns}{}^{ij}$ in terms of the known or determined quantities. Referring to the definition of the ratio $m^{ij}=(T_L+T_{ns}{}^{ij})/(T_S+T_{ns}{}^{ij})$ in Equation 11, $m^{ij}$, $T_L$, and $T_S$ are determined values. Thus, substituting the expressions for $T_L$ and $T_S$ (from Equations 16 and 17) into the definition of $m^{ij}$, $T_{ns}{}^{ij}$ may be expressed as $$T_{ns}{}^{ij}=[(n-m^{ij})(T_{PL}-T_{PS})]/[(m^{ij}-1)(n-1)]. \tag{18}$$

In state 452 that follows, the process 430 determines the various components of the measured signals in terms of known or previously determined quantities according to Equations 4a–h. The process 430 stops at an end state 454.

The process 430 performed in the foregoing example manner determines the components of the measured signals $A_{BL}$, $A_{BS}$, $A_{DL}$, $A_{DS}$ of the four frames of the calibration set. The components comprise the quantities listed on the left sides of Equations 4a–h, and can be classified into four categories according to their dependencies on the incident light intensity I (which is proportional to the detector signal $W_{ie}$) and time T. As previously described in reference to FIG. 3, there are four dependency combinations given the two parameters I and T: (1) depends on both I and T, (2) depends on I but not T, (3) depends on T but not I, and (4) independent of I and T. Referring to FIG. 6, one can see that the first components of each frame, namely $A_{L1}$ and $A_{S1}$, depend on both I (via $W_{ie}$) and T. Specifically, $A_{L1}$ differs from $A_{S1}$ by the difference in the integration times $T_L$ and $T_S$; the level of $W_{ie}$ (representative of I) can change the values of both $A_{L1}$ and $A_{S1}$. The second components of each frame, namely $A_{L2}$ and $A_{S2}$, do not depend on time T (hence both being equated to and represented simply as $A_2$ above), but depend on I for the same reason as that of the first components. The third components of each frame, namely $A_{L3}$ and $A_{S3}$, do not depend on I by definition (of dark signal), but depend on time T for the same reason as that of the first components. The fourth components, namely $A_{L4}$ and $A_{S4}$, do not depend on I because they accumulate during the idle periods in the absence of light, and also do not depend on T when the idle periods (and their temporal sub-structures) are substantially similar for the long and short frames.

It will be understood that the dark signal subtraction and flat-fielding techniques previously described in reference to FIG. 2 may be performed without the foregoing four-components analysis. In such techniques, only a baseline and dark frames (preferably of same duration) are needed. Hence, the first and second components ($A_{L1}$ and $A_{L2}$; $A_{S1}$ and $A_{S2}$) are not distinguished, but rather lumped into a single "baseline" component. Similarly, because no effort is made to determine the actual dark signal duration, thus resolving it from the idle signal, the third and fourth components ($A_{L3}$ and $A_{L4}$; $A_{S3}$ and $A_{S4}$) are not distinguished, but rather lumped into a single "dark" component.

It should be apparent that resolving the baseline (e.g., flat-fielding) frame and dark frame signals into more components allows one to better understand in general the composition of the measured signals. Such an advantage is particularly desirable if such components can be analyzed without a substantial modification to an existing configuration. Another advantage afforded by such components analysis relates to better configuring the manner in which measurements are performed, based on the understanding of the components. For example, if the integration time nonuniformity $T_{ns}{}^{ij}$ is shown to be significant, then the shutter or the manner in which the shutter is operated may be configured differently so as to reduce such effect and thereby improving the quality of the measurement. In another example, if the idle component $A_4$ is found to be significant, the profile of the idle period may be modified to reduce the magnitude of the idle component, thereby again improving the quality of the measurement.

Figure 9:
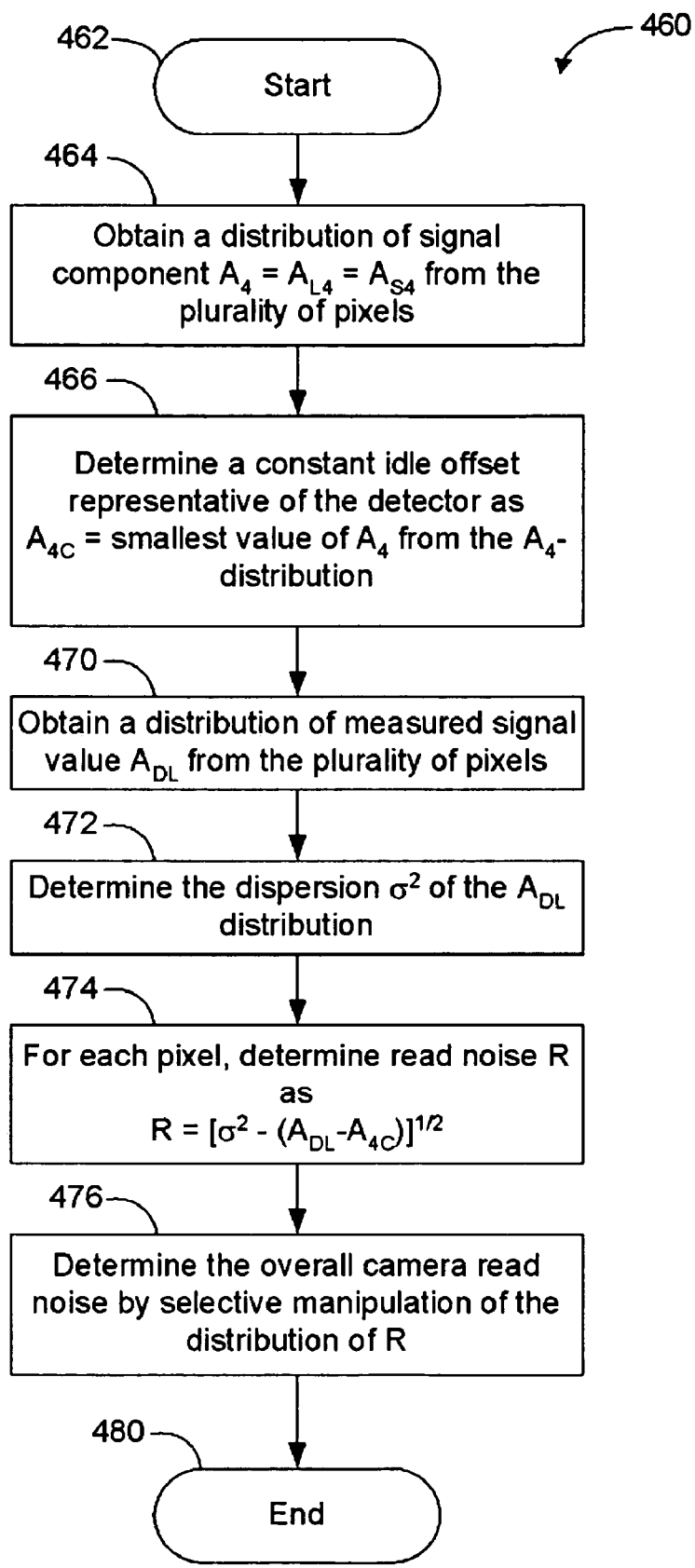
FIG. 9 illustrates an example process that utilizes some of the determined component related quantities to characterize an error quantity associated with a detector.

One advantageous application where the knowledge of the idle component $A_4$ is useful relates to determination of the camera's read noise. FIG. 9 illustrates an example process 460 that characterizes a read noise associated with the pixels, as well as the overall read noise of the camera.

The process 460 begins in a start state 462. In state 464 that follows, the process obtains a distribution of the idle component $A_4$ from each of the pixels. In state 466 that follows, the process 460 determines a constant idle offset $A_{4C}$ representative of the detector by selecting the smallest value of $A_4$ from the $A_4$-distribution. Steps in states 464 and 466 are generally analogous to the steps in states 442 and 444 of FIG. 8, where a value of $m^{ij}$ from the $m^{ij}$-distribution was selected to be representative of the detector.

In state 470 that follows, the process 460 obtains a distribution of measured signal values (dark long) $A_{DL}$ from the plurality of pixels. In state 472 that follows, the process 460 determines the dispersion $\sigma^2$ of the $A_{DL}$-distribution. The dispersion $\sigma^2$ may depend on the properties of the distribution, and may be determined in a known manner. In state 474 that follows, the process 460 determines, for each pixel, a read noise R as $$R=[\sigma^2-(A_{DL}-A_{4C})]^{1/2}. \tag{19}$$

In state 476 that follows, the process 460 determines an overall camera read noise by selective manipulation of the resulting distribution of R. For example, an average value of R may be selected to represent an average read noise for the detector. The process stops at an end state 480.

Based on the foregoing description, it should be apparent that the concept of varying different operating parameters and measuring signals for corresponding variations allows one to resolve the measured signals into various components that have different dependencies on the operating parameters. Such a concept can be extended to include more than the two operating parameters (I and T) without departing from the spirit of the present teachings.

Alternatively, one of the four components of for each frame may be resolved further in terms of subcomponents of the detector signal W and time T parameters. For example, as illustrated in FIG. 6, the $A_4$ component (labeled as $A_{L4}$ and $A_{S4}$) is depicted as having an example L-shaped substructure. Such substructure may be determined by $W_{dc}$, $T_{delay}$, $T_{shiftout}$, and $W_{PN}$, where the subscript "PN" represents pattern noise. The pattern noise signal magnitude $W_{PN}$ may further be resolved as a sum of a spurious charge signal magnitude $W_{SC}$ and an effective on-chip amplifier dark signal magnitude $W_{EDC}$. Thus, such a substructure may be analyzed in the spirit of the present teachings, so as to allow one to distinguish and quantify the aforementioned substructure defining quantities.

The foregoing analysis of the calibration frame comprising the baseline and dark frames (with each comprising the long and short integrations) yields various components associated with each pixel. These components are summarized as follows (reference to FIG. 6 helpful):

TABLE 1

| Component | Symbol Long | Symbol Short | Depends on (Intensity and/or integration time) | Useful for |
|---|---|---|---|---|
| Baseline | $A_{L1}$ | $A_{S1}$ | Both | Normalizing pixels' responses |
| Shutter error | $A_2$ | $A_2$ | Intensity | Removing shutter nonuniformity |
| Dark signal | $A_{L3}$ | $A_{S3}$ | Integration time | Removing contribution from dark signal |
| Idle | $A_4$ | $A_4$ | Neither | Removing contribution during readout |

As previously described, the calibration frames being measured temporally proximate the data frames (as shown in FIG. 4) allows the various components of the calibration to be obtained under similar conditions as that of the data. As also previously described, certain embodiments of the measurement system advantageously utilize the long-short combination of integration times. Such a configuration allows at least some of the calibration components to be resolved in integration time-dependent term(s).

Figure 10A:
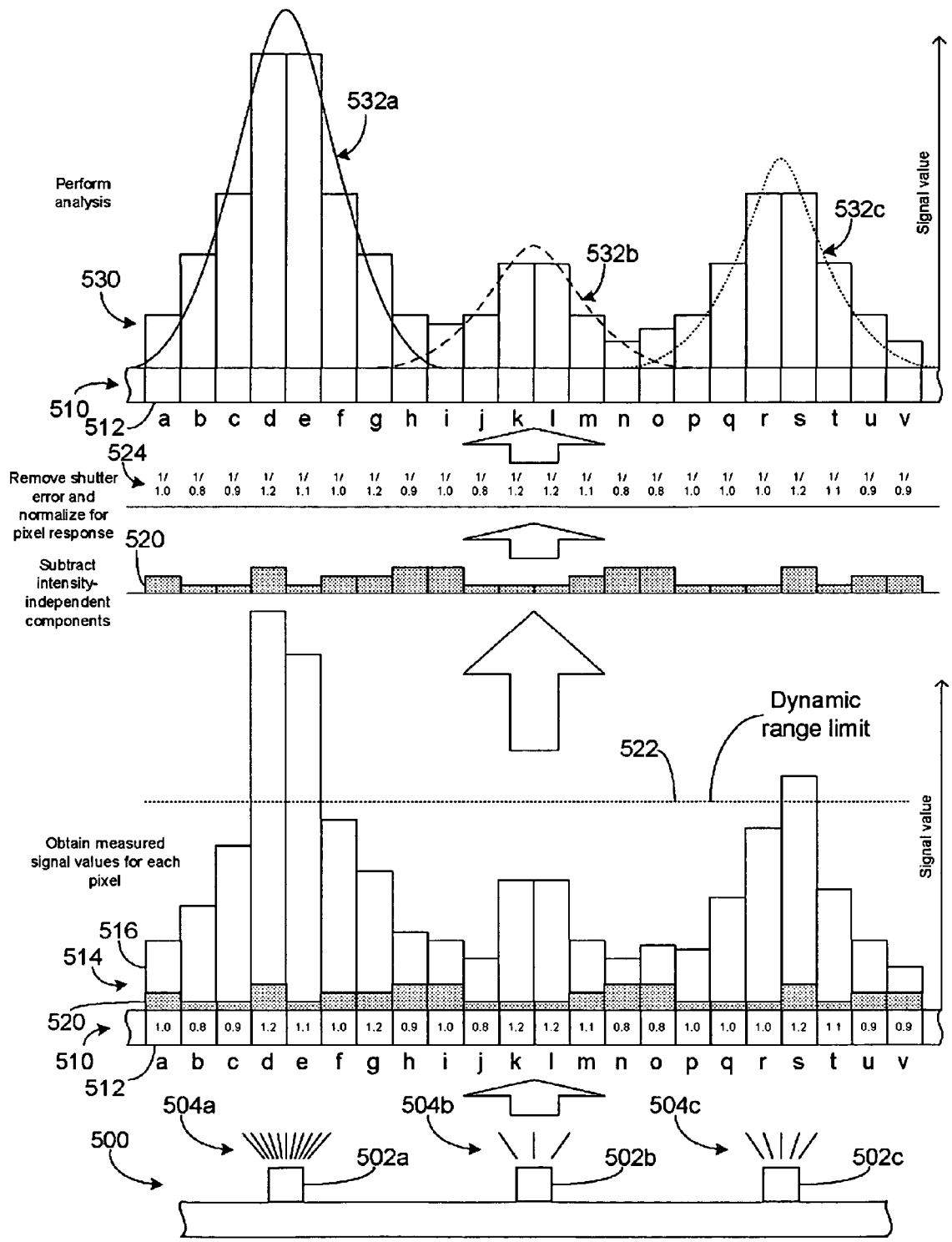
FIG. 10A illustrates an example signal processing process wherein the signal is measured from an array-type sample and processed to remove and correct for various components of the signal.

Once the four calibration components are obtained proximate a set of measured data, the components can be applied to the measured data to yield a corrected data. FIGS. 10A and B illustrate some example biological measurements that undergo such a correction.

FIG. 10A illustrates a portion of an array-type device 500 having a plurality of probes 502a–c. In certain applications, such probe preferentially attracts a specific sequence of nucleotides (strand). The relative number of such strands adhered to the probe is indicative of the relative concentration of that particular strand in a sample. To determine the relative number of a strand adhered to a given probe, the strands may be tagged with tags that emit detectable energy upon excitation. Thus, the example strand-laden probes 502a–c are depicted as emitting energy 504a–c respectively, with varying intensities. The emitted energy 504a is depicted as being more intense than that of 504c, which in turn is more intense than 504b.

Such data can be measured via a segmented detector 510, such as a CCD, having a plurality of pixels 512 (denoted as pixels 512a–v) to yield a measured signal value 514 for each pixel. The measured signal value includes the contribution from the actual incident energy from the array, as well as other contributions. Such other contributions include contributions associated with the four components determined above.

In FIG. 10A, the measured signal value 514 is depicted as comprising an intensity-independent portion 520 and an intensity-dependent portion 516. It will be understood that such delineation is for descriptive purpose, and is generally not apparent from the measured signal value alone.

FIG. 10A also depicts a dynamic range limit 522 associated with the example detector 510. One can see that pixels 512d, e, and s have measured signals that exceed the dynamic range limit 522. As described in the above incorporated reference (U.S. Pat. No. 6,894,264), such limitations may be mitigated by utilizing the signal from the short integration and appropriately scaling it. Thus, although some of the measured signal values are depicted to exceed the limit 522, it will be assumed to be "scalable" for the purpose of description herein.

FIG. 10A also illustrates the pixels 512a–v having relative response values assigned to them. As previously described, the pixels in a given detector may respond differently to the substantially same input of energy. For the purpose of description, a reference response value is selected to be 1. As examples, the example response value assigned to pixel 512a is 1.0; thus, pixel 512a responds with approximately 100% of the expected reference value. The example response value assigned to pixel 512b is selected to be 0.8; thus, pixel 512b under-responds with approximately 80% of the expected reference value. The example response value assigned to pixel 512d is selected to be 1.2; thus, pixel 512d over-responds with approximately 120% of the expected reference value. The example response values associated with the pixels 512a–v may be obtained by comparing the baseline values ($A_{L1}$ or scaled $A_{L1}$). An average baseline value may be assigned a reference response value of 1, and each pixel's baseline value may be compared to the average baseline value to yield its response value.

The measured signal values 514 may have subtracted from it the intensity-independent portion 520. For the four components summarized in Table 1 (and illustrated in FIG. 6), the intensity-independent portion 520 comprises the dark signal ($A_{L3}$ or scaled $A_{S3}$) and idle component ($A_4$).

Following the subtraction of the shutter error $A_2$ may be removed from the signal value. At this stage, the signal value (for the long integrations) can be represented as (referring to FIG. 6) $W(T_L+T_{ns}^{ij})$, where W is the pixel signal due to the incident energy from the sample being measured. For the short integrations, the signal value can be represented as $W(T_S+T_{ns}^{ij})$. The pixel signal W is in turn generally proportional to the intensity of the incident energy from the sample being measured. The values of $T_L$, $T_S$, and $T_{ns}^{ij}$ can be determined in terms of known values, as described above in reference to Equations 16–18. From the foregoing determination, the shutter error $A_2$ can be determined to be a fraction $T_{ns}^{ij}/(T_L+T_{ns}^{ij})$ (for long, and $T_{ns}^{ij}/(T_S+T_{ns}^{ij})$ for short) of the signal value at this stage. Once determined, the shutter error $A_2$ for each pixel can be removed from that pixel's signal value.

Following the removal of the shutter error, the remaining signal value for a given pixel is approximately representative of the energy intensity incident on that pixel. At this stage, the pixels' responses can be normalized such that the measurement values obtained from the pixels are advantageously "on par" with each other. As described above, the pixels 512a–v have example response values associated with them. One way to normalize a given pixel's signal value is to multiply the signal value by an inverse of that pixel's response value. Thus for pixel 512a, the example normalization factor is approximately 1/1.0=1.0. As examples, for pixel 512b, the example normalization factor is approximately 1/0.8=1.25. Note that this compensates for the under-response of pixel 512b. For pixel 512d, the example normalization factor is approximately 1/1.2=0.83. Note that this compensates for the over-response of pixel 512d.

After the foregoing corrections to the measured signal value for a given pixel, a corrected signal value 530 is obtained for that pixel. The resulting corrected signal values for the pixels of the detector can be analyzed further. For example, curves can be fit to the values of the pixels' output, as depicted by example Gaussians 532a–c. The Gaussian curve 532a represents the detected energy 504a from the probe 502a; the Gaussian curve 532b represents the detected energy 504*b* from the probe 502*b*; and the Gaussian curve 532*c* represents the detected energy 504*c* from the probe 502*c*. The unfolding of the curves 532*a–c* at the overlapping regions (pixels 512*h, j, o* in FIG. 10A) may be performed via any number of curve fitting/analysis methods.

From the example measured (raw) signal distribution 514 and the corrected signal distribution 530, one can readily see that the raw distribution would yield fitted curves having erroneous results. For example, the example pixel 512*d* has a relatively high dark signal level and also a relatively high response value. As a result, the relatively high value of the uncorrected signal for pixel 512*d* would skew the fit towards the left side of the distribution. Such a fit would yield an erroneous peak value and possibly other erroneous curve parameter(s). In another example, the relatively high value of the uncorrected signal for pixel 512*s* would skew the fit towards the right side of the distribution.

Figure 10B:
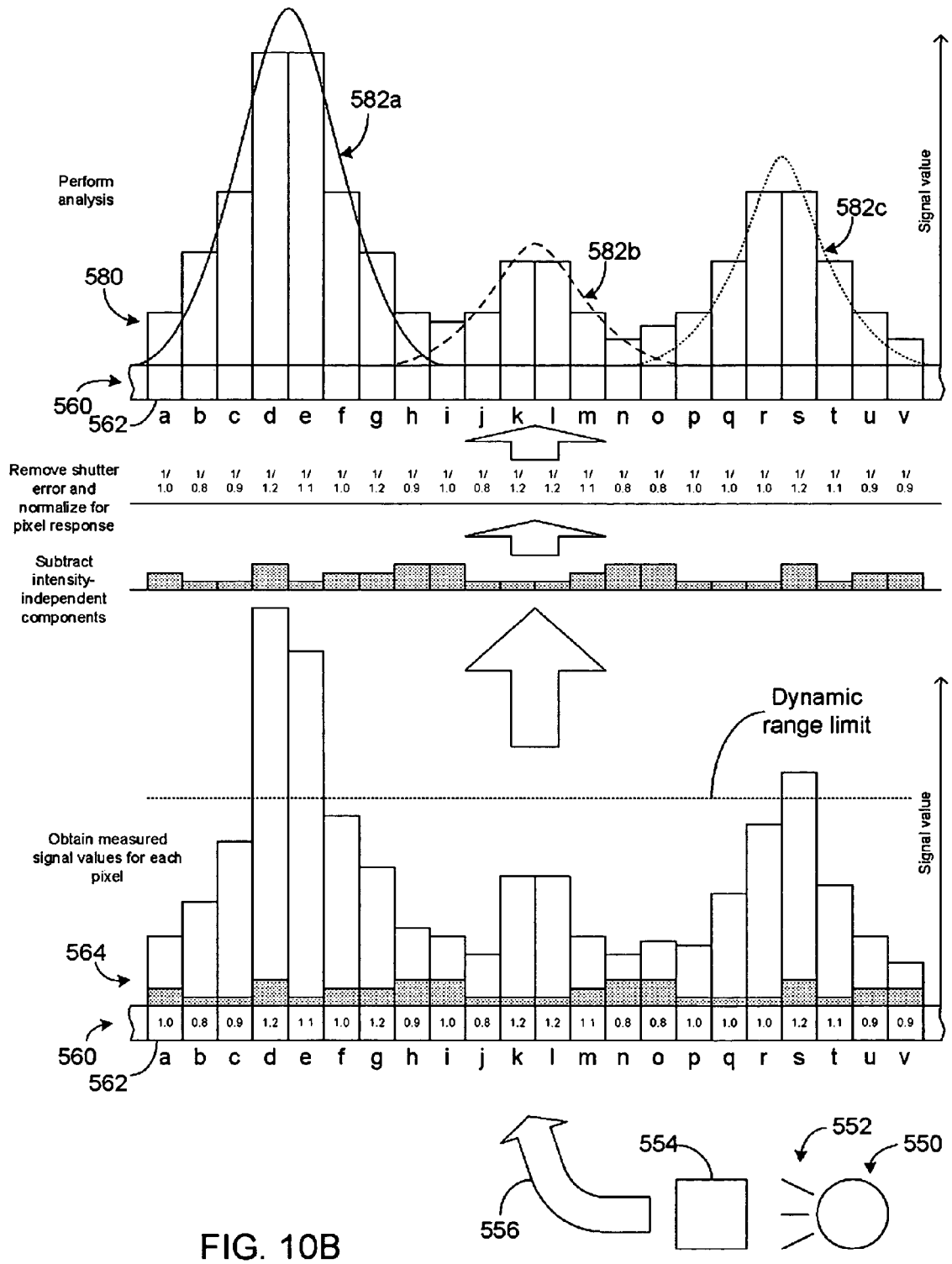
FIG. 10B illustrates another example signal processing process wherein the signal is obtained from a relatively localized sample and dispersed spatially so as to be detectable by a position sensitive pixelated detector.

FIG. 10B now illustrates a similar data correction process where a measured raw signal distribution 564 from a plurality of pixels 562*a–v* of a detector 560 can be processed to yield a corrected distribution 580. Curves 582*a, b*, and *c* can be fit and analyzed further in a similar manner. The measured raw data 564 is depicted to arise from a relatively localized source 550 that emits energy 552 in response to some form of excitation. The emitted energy 552 from the localized source can pass through an optical element 554 to yield the measured distribution 564. In certain embodiments, the measurement system may comprise a spectrometer based device, and the optical element 554 may comprise a wavelength dispersing device such as a prism, various types of diffraction gratings, and the like. For such a system, the wavelength separation is depicted in FIG. 10B as an arrow 556. Such a measurement system may be utilized to measure relative abundances of particular nucleotide strands tagged with tags that emit light having particular colors.

As one can see, the distributions of data in their various stages are essentially left unchanged between FIGS. 10A and B. Such depiction is for descriptive purpose, and in no way intended to limit the scope of the present teachings in any manner. It will be appreciated that once a biological measurement system generates a detectable energy that is somehow distributed in space at the detector, the segmented detector can detect that energy using its plurality of pixels. The various pixel-related and other corrections can then be applied to the pixels-detected and measured signals in a manner described above.

Figure 11:
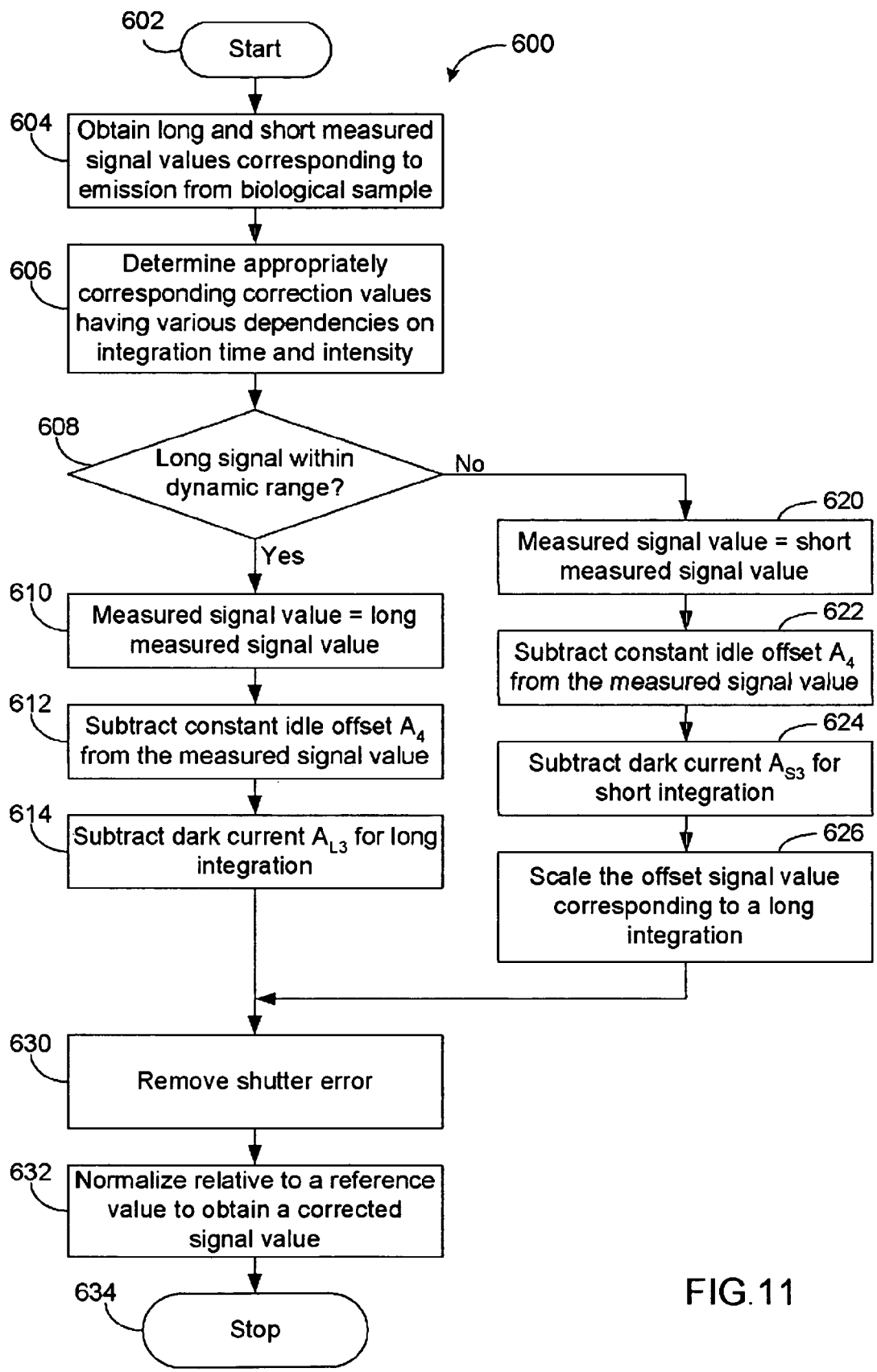
FIG. 11 illustrates an example process for performing the signal processing of FIGS. 10A and B.

FIG. 11 now illustrates a process 600 that summarizes the biological measurement configurations described above in reference to FIGS. 10A–B. The process 600 is for a given pixel; thus, such process for other pixels can be performed in a similar manner, either sequentially, concurrently, or any combination thereof. Moreover, the process 600 describes how long and short measured signals can be advantageously incorporated into the analysis.

The process 600 begins as a start step 602, and in step 604 that follows the process 600 obtains long and short measured signal values corresponding to emissions from a biological sample. In step 606 that follows, the process 600 determines the appropriately corresponding correction values having various dependencies on integration times and intensity. That is, a set of four components for the long and short frames determined as described above are assigned to appropriately proximate set or sets of data frames. It will be understood that step 606 may be performed after (as shown in FIG. 11) or before step 604. That is, calibration frames can be obtained after or before measurement of the sample.

In a decision step 608 that follows, the process 600 determines whether the long measured signal value is within the dynamic range. If "yes," then the process 600 proceeds to step 610, where it assigns the long signal value as the measured signal value. In step 612 that follows, the process subtracts the substantially constant idle offset $A_4$ from the measured signal value. In step 614 that follows, the process 600 subtracts the dark signal component $A_{L3}$ obtained from the long integration.

If the answer to the decision step 608 is "no," the process 600 proceeds to step 620*m* where it assigns the short signal value as the measured signal value. In step 622 that follows, the process subtracts the substantially constant idle offset $A_4$ from the measured signal value. In step 624 that follows, the process 600 subtracts the dark signal component $A_{S3}$ obtained from the short integration. In step 626 that follows, the process 600 scales the offset signal value corresponding to a long integration. Such scaling causes the scaled value to advantageously exceed the dynamic range limit. The scaling process in step 626 may be performed by a separate process that is invoked by the process 600.

With the offset signal value being either from the unscaled long signal (from step 614) or the scaled short signal (from step 626), the process 600 in step 630 removes the shutter error $A_2$. In step 632 that follows, the process 600 normalizes the signal value relative to a reference value to obtain a corrected signal value. The process 600 ends at a stop step 634.

FIGS. 12–15 now show that various signal components and temporal quantities associated with the herein-described long/short and baseline/dark frames can be used to characterize a portion or all of one or more detectors. Such characterization can be used to ensure that a given detector will respond in a predictable manner for a given operating condition. Such characterization can also be used as a quality control technique when fabricating the detectors and/or instruments having such detectors.

Figure 12:
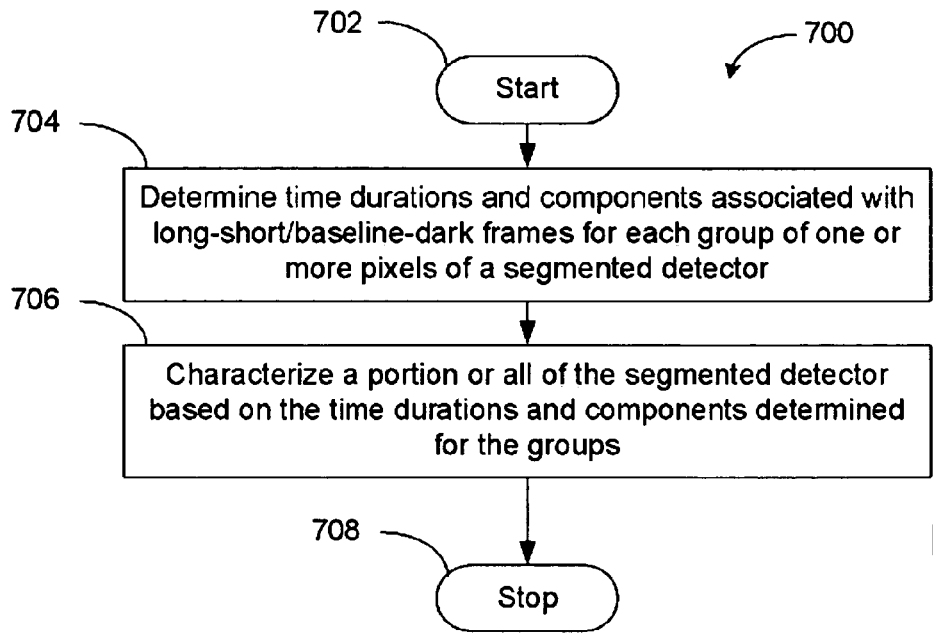
FIG. 12 illustrates one embodiment of an example process that utilizes at least some of the determined component related quantities to characterize a portion or all of a detector.

FIG. 12 shows one embodiment of a process 700 that describes a generalized form of detector characterization based on the signal components and/or temporal quantities. The process 700 begins in a start state 702, and in step 704, the process 700 determines one or more temporal quantities and/or one or more signal components associated with the long/short and baseline/dark frames. Such determinations are described herein. In one embodiment, the temporal quantity(ies) and/or the signal component(s) are determined for bins having one or more pixels of a segmented detector. As is known, such binning can reduce the time required for reading out and processing. In some embodiments, binned pixels may provide sufficient resolution for the purpose of detector characterization. The process 700 then, in step 706, characterizes a portion or all of the segmented detector based on the temporal quantity(ies) and/or the signal component(s). The process 700 ends at a stop state 708.

Figure 13A:
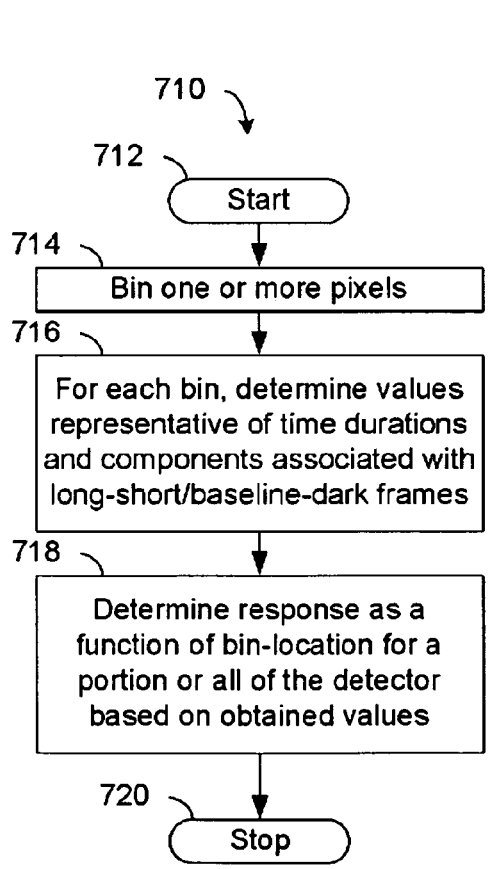
FIG. 13A illustrates one example of the process of FIG. 12, where the portion or all of the detector is characterized for response as a function of location of bins having one or more pixels.
Figure 13B:
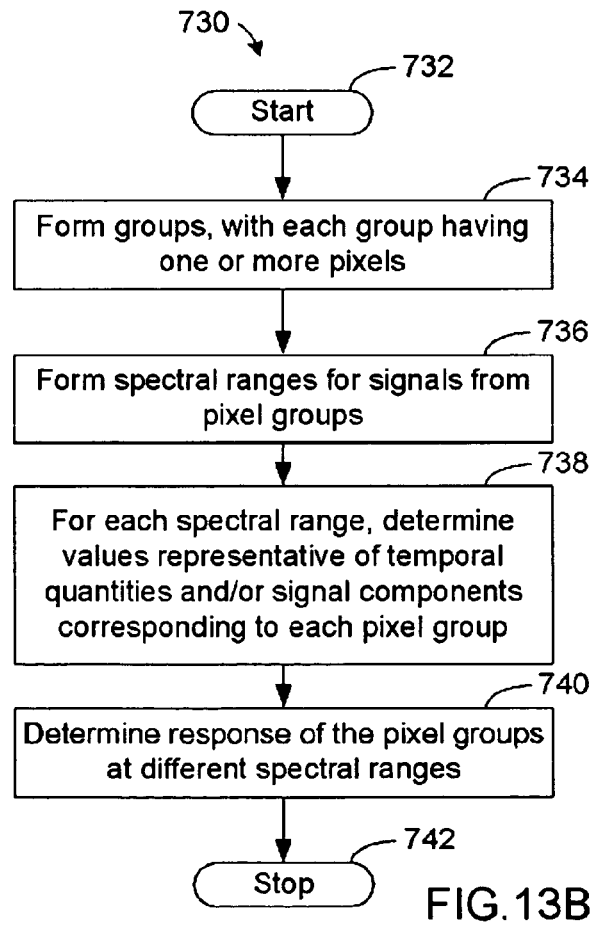
FIG. 13B illustrates another example of the process of FIG. 13, where the portion or all of the detector is characterized for response as a function of location of bins having one or more pixels.

FIGS. 13A and 13B show two examples of the process 700 described above in reference to FIG. 12. FIG. 13A shows one embodiment of an example process 710 that determines a response of a segmented detector as a function of the location of bins having one or more pixels. The process 710 begins in a start state 712, and in step 714, it groups the pixels into bins so that each bin includes one or more pixels. In step 716, the process 710 determines, for each bin, values representative of one or more temporal quantities and/or one or more signal components. In step 718, the process 710 determines a response of the segmented detector based on the determined values as a function of the location of the bins. The process 710 ends at a stop state 720.

FIG. 13B shows one embodiment of a generalized example process 730 that determines a response of a segmented detector. Such a response can include spectral and/or spatial responses. The process 730 begins in a start state 732, and in step 734, it groups the pixels so that each group includes one or more pixels. In step 736, the process 730 forms spectral ranges for signals associated with the grouped pixels. In step 738, the process 730 determines, for each group of pixels, values representative of one or more temporal quantities and/or one or more signal components that can be determined as described herein. Such values can be determined for each of the spectral ranges. In step 740, the process 730 determines a response of the segmented detector based on the values for the pixel groups obtained at different spectral ranges. The process 730 ends at a stop state 742.

An example response from an example segmented detector is described below in greater detail.

Figure 14:
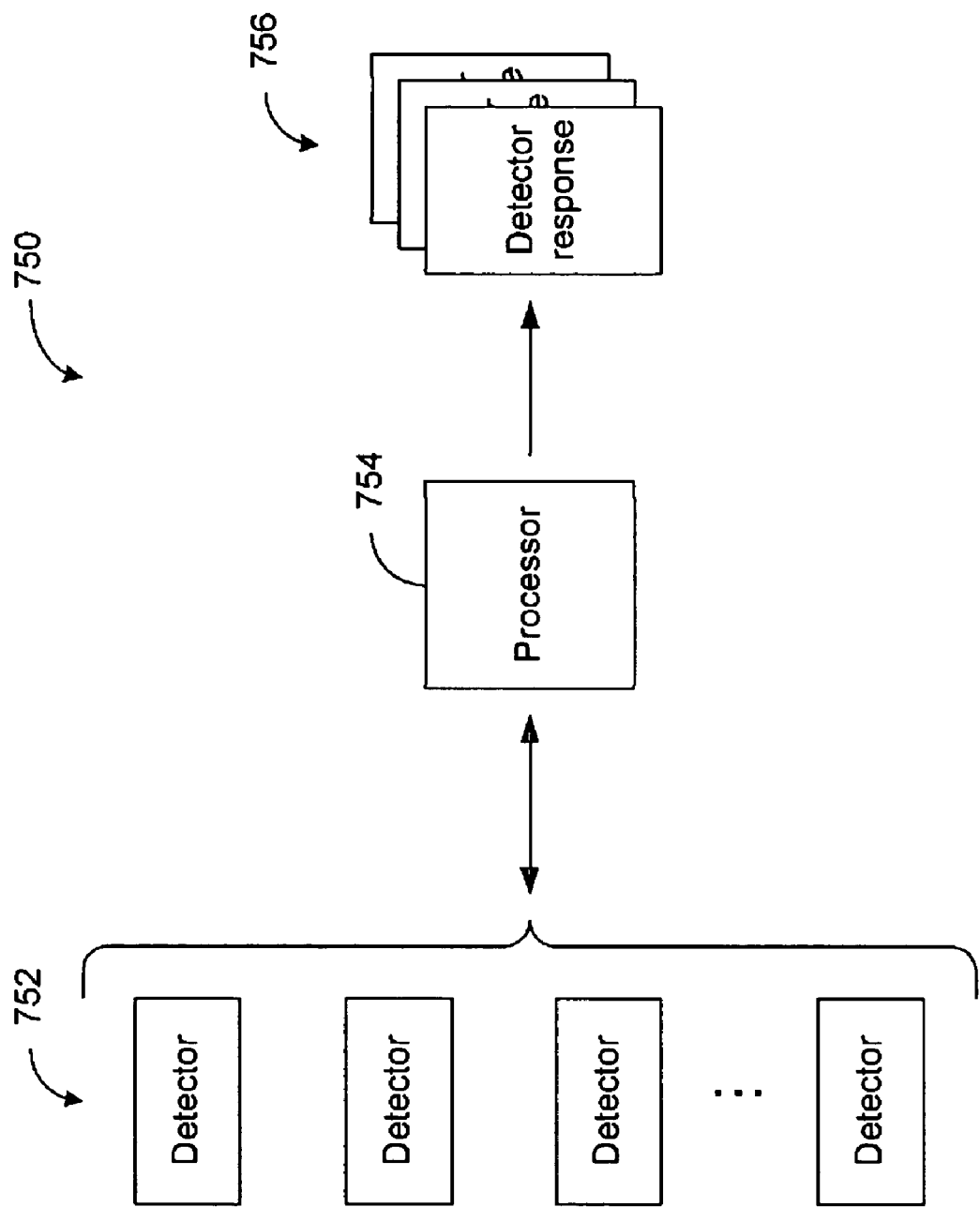
FIG. 14 illustrates a block diagram of an example configuration where one or more detectors can be characterized for one or more responses based on one or more component related quantities.

The detector characterization processes described above in reference to FIGS. 12–13 can be applied to one or more detectors. FIG. 14 shows one embodiment of an example configuration 750 where a plurality of detectors 752 are being characterized by a processor 754. Such characterization can yield one or more detector responses 756.

FIGS. 15A–15F now show by example various representations of various values described above in reference to the example characterizing process 730 described above in reference to FIG. 13B. The example representations were obtained from an example CCD having 512×512 pixels. Pixels were grouped into 5×5 pixel groups. For each 5×5 pixel group, the center 3×3 pixels were read out, and the edge pixels (of the 5×5 pixel group) were not read out. Thus, the 3×3 read-out pixel sub-groups were separated from each other by 2-pixel wide gaps. The operating spectral range of the example CCD was divided into 20 ranges. Thus, the example plots shown represent 20 (spectral) by 96 (spatial) representations. The long integration time was approximately 300 ms, and the short integration time was approximately 60 ms. For the purpose of description of the foregoing example CCD characterization, the long frames (approximately 300 ms integration time) responses are shown. It will be understood that responses corresponding to short frames will generally appear similar, but with lower amplitudes.

Figure 15A:
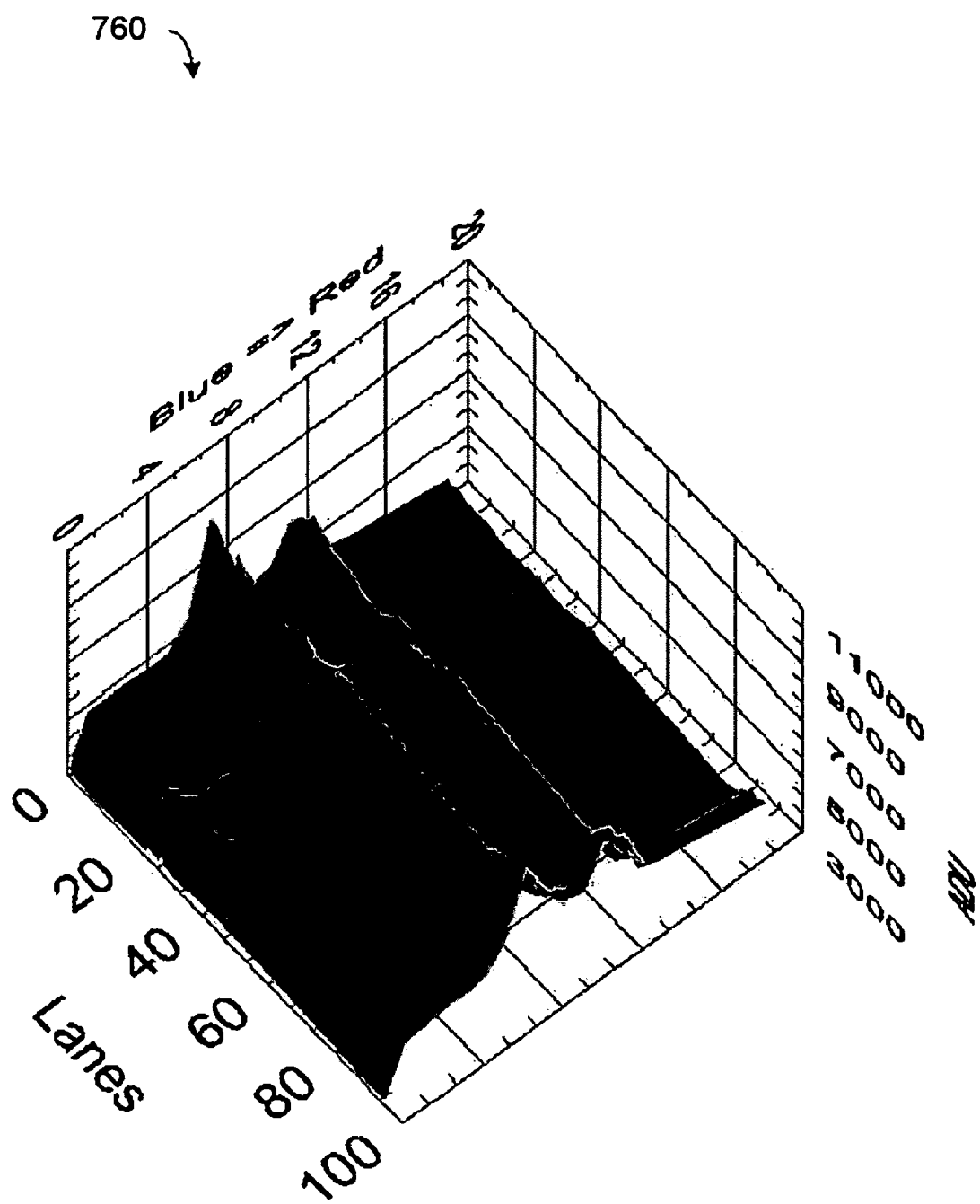
FIGS. 15A–15F illustrate examples of responses of various component related quantities for a given detector.

FIG. 15A shows an example response 760 of the example 96 lanes. In particular, values obtained from the lanes correspond to a measured long baseline frame ($A_{BL}$ described above in reference to Equation 2a). If the measured value cannot be resolved into various signal components, the example response 760 essentially represents substantial limit on characterizing the detector. However, as described herein, the long baseline measured signal can be resolved into various individual components or some combinations thereof. Also, as described herein, the use of dark frames allows one to obtain at least some information about the composition of baseline frames. Such resolving techniques allow characterization beyond the baseline-characterization level, thereby providing a substantially more flexible manner for detector characterization.

Figure 15B:
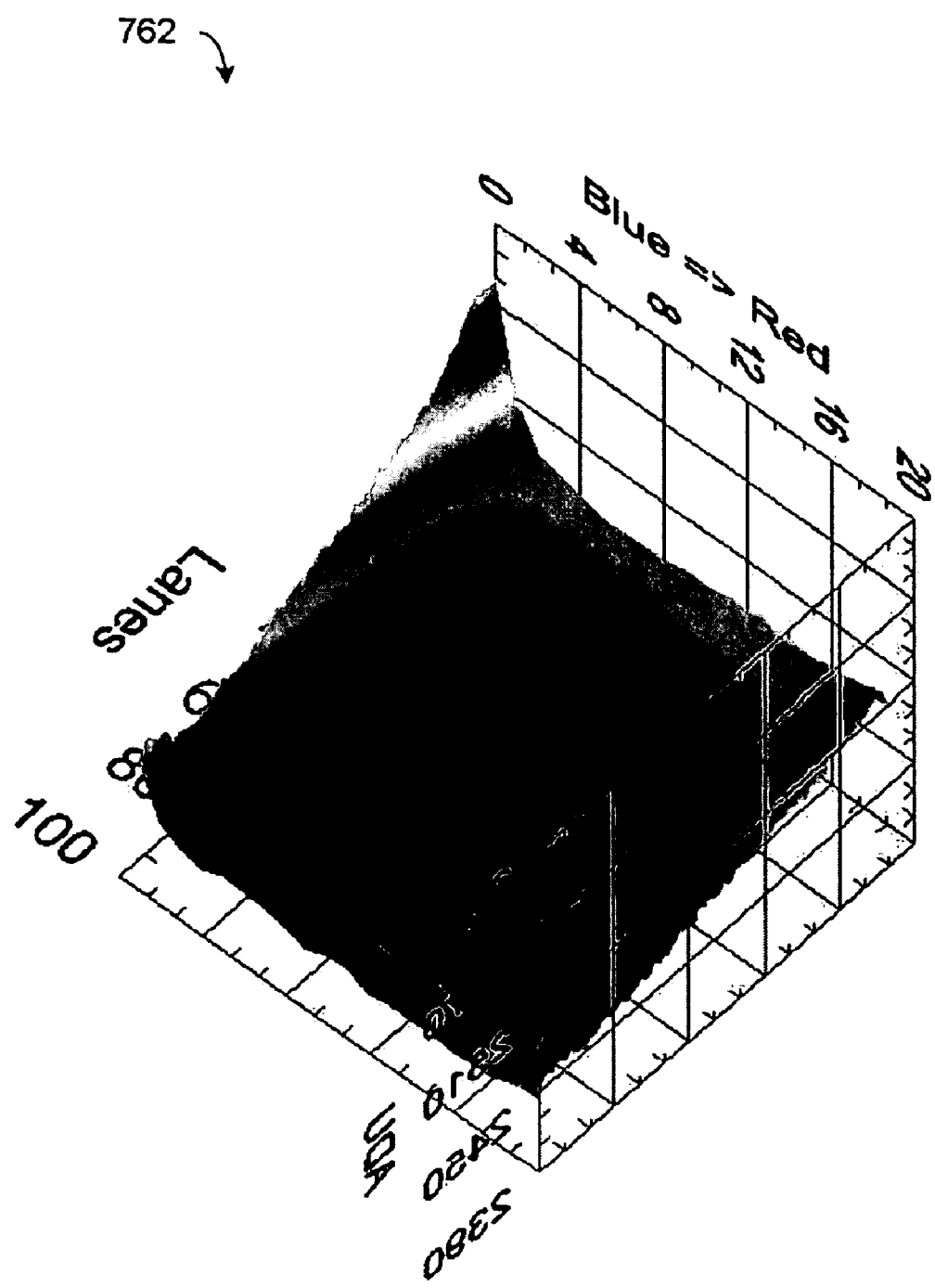

FIG. 15B shows an example response 762 corresponding to one such characterization beyond the baseline level. The example response 762 corresponds to the dark counterpart ($A_{DL}$ described above in reference to Equation 2a) to the baseline frame. In one embodiment as described herein, the quantity $A_{DL}$ includes information about the detector's dark signal and readout contributions. As shown in FIG. 15B, one can readily see that the detector's response without light input is substantially different than that with light. Even without having to rely on possible mechanisms for such differences, one can see that detector characterization at an empirical level is provided with a substantially greater flexibility by using the baseline/dark and long/short frame combinations.

Figure 15C:
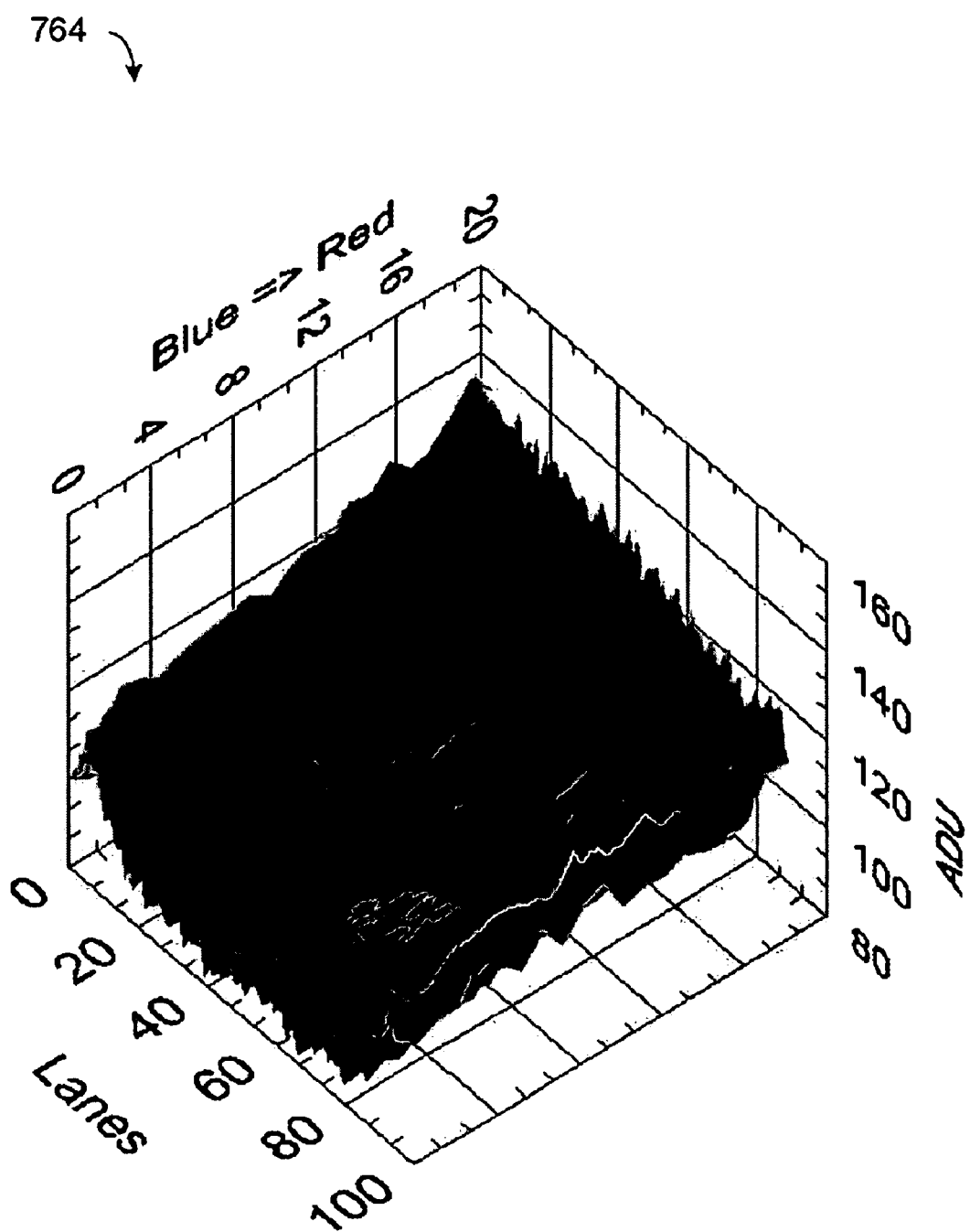
Figure 15D:
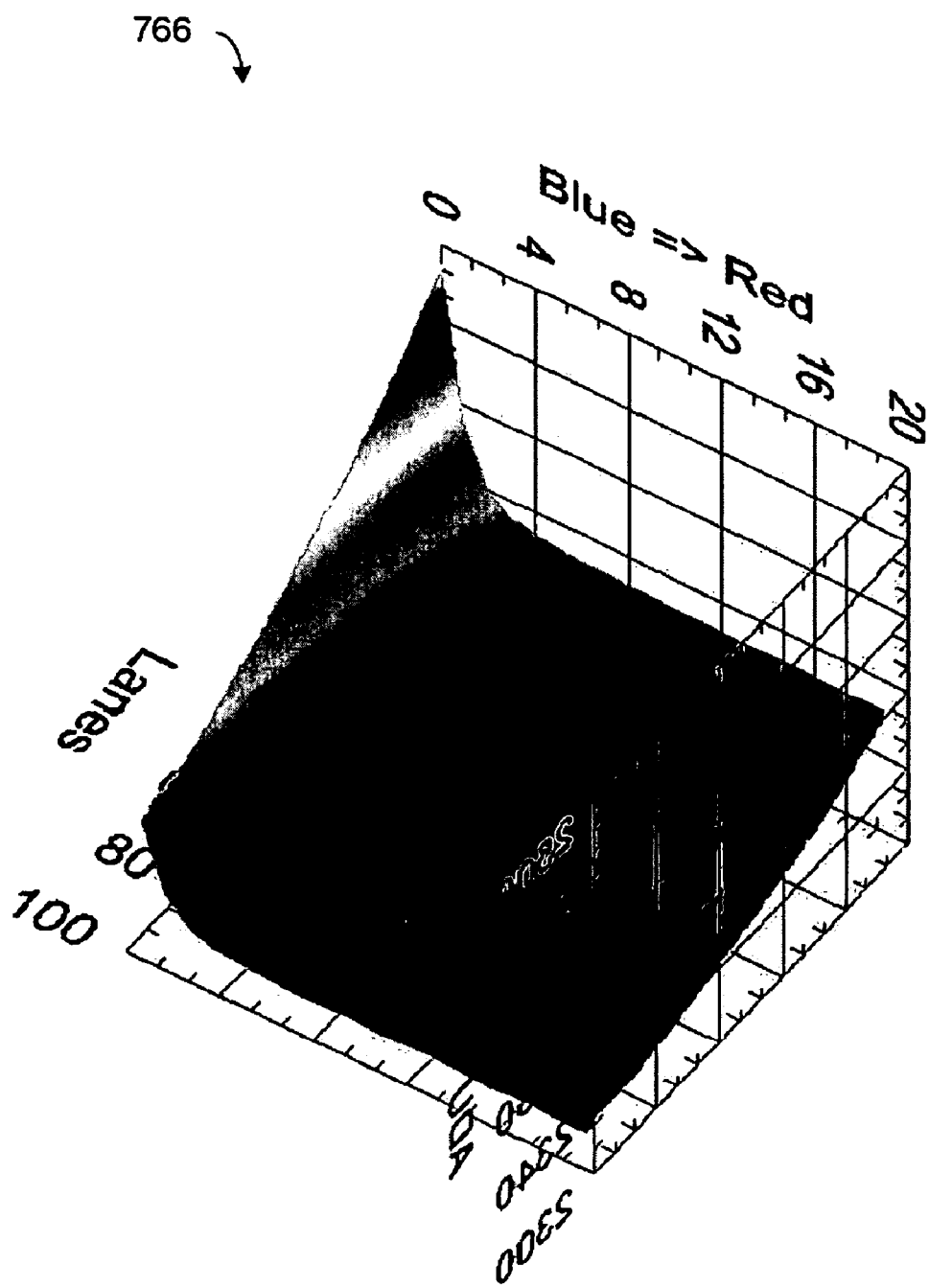

As described above in reference to FIG. 15B, the dark frame value $A_{DL}$ includes contributions from the detector's dark signal and readout. FIG. 15C shows a response 764 corresponding to the resolved dark signal contribution ($A_{L3}$) to the dark frame response 762 of FIG. 15B. FIG. 15D shows a response 766 corresponding to the resolved readout contribution ($A_4$) to the dark frame 762 of FIG. 15B.

In one embodiment as described herein, removal of the dark signal component ($A_{L3}$) and the readout component ($A_4$) from the baseline frame ($A_{BL}$) leaves contributions from $A_{L1}$ and $A_{L2}$. The quantity $A_{L1}$ represents the resolved component due to the baseline light incident on the detector. The quantity $A_{L2}$ can be determined as a product $W_{ie} T_{ns}^{ij}$, and represents the contribution during the calibration signal intensity transition time ($T_{ns}^{ij}$). Both $T_{ns}^{ij}$ and $W_{ie}$ (detector signal value during baseline frame) can be determined as described herein.

Figure 15E:
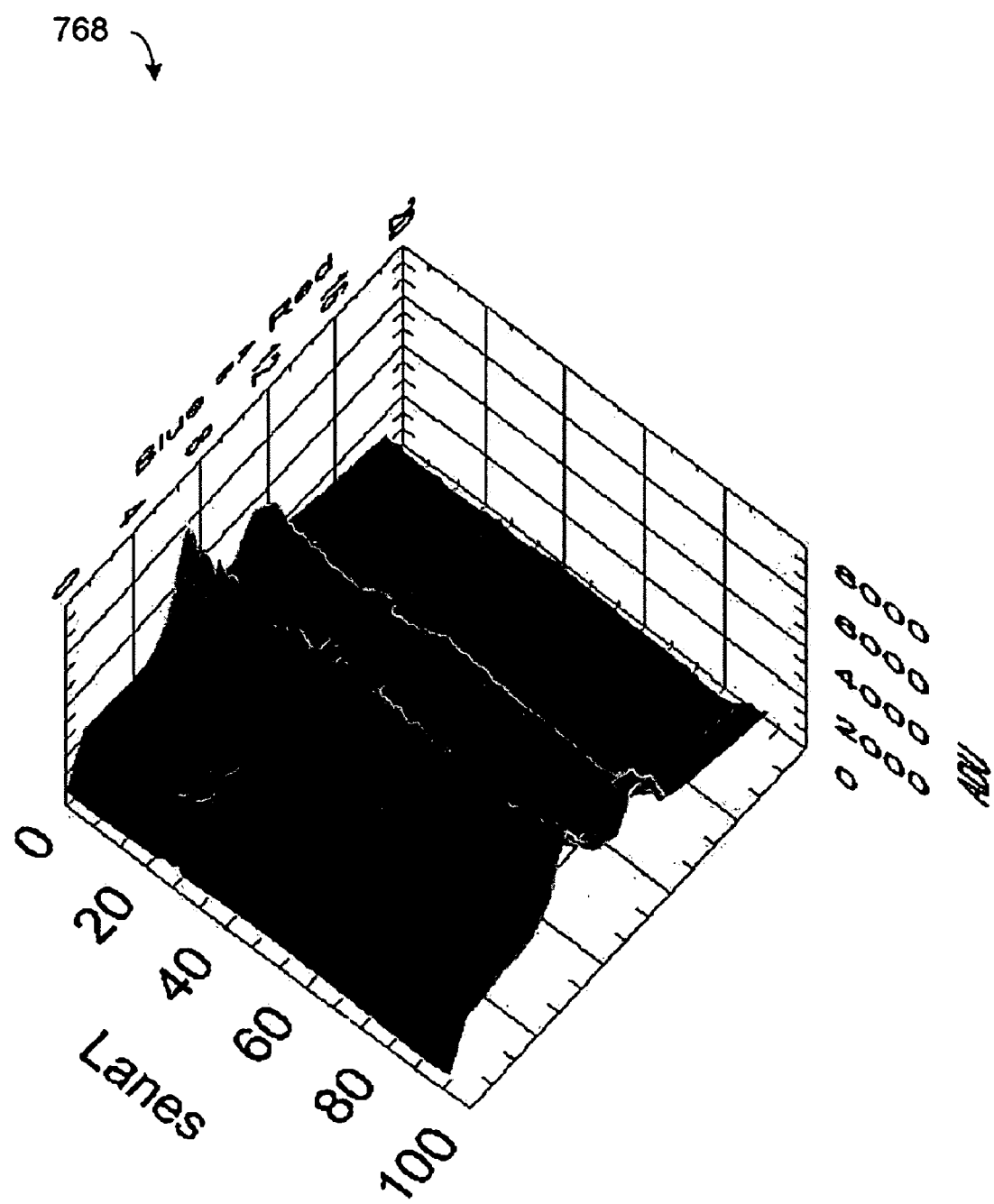
Figure 15F:
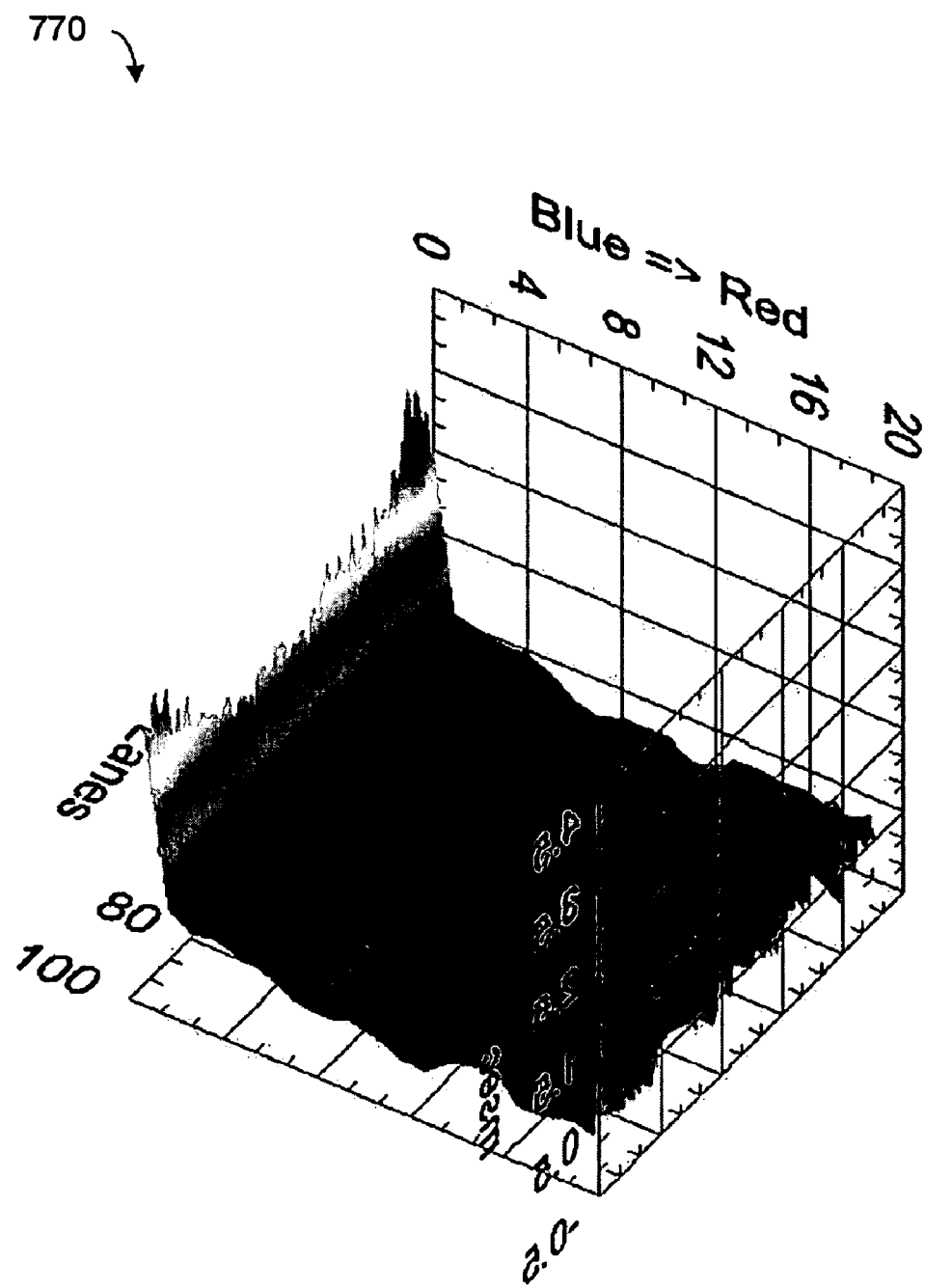

FIG. 15E shows a response 768 corresponding to the resolved component $A_{L1}$ due to the baseline light incident on the detector. FIG. 15F shows a response 770 corresponding to the resolved transition time value $T_{ns}^{ij}$. Although not shown, responses corresponding to other components or values (e.g., $W_{ie}$, $A_{L2}$), or any combination thereof, can be determined.

In the example responses shown in FIGS. 15A–15F, the example detector as a substantially whole is characterized. It will be understood that similar characterization can be performed on a selected portion of the detector.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated may be made by those skilled in the art without departing from the scope of the present invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A method of performing a biological assay using a detector comprising a plurality of pixel elements configured to resolve signal emissions arising from a biological sample, the method comprising:

evaluating a plurality of response signals generated by each of the pixel elements resulting from exposure to a calibration signal while varying the intensity of the calibration signal in combination with varying of an acquisition time of the pixel elements;

identifying systematic signal deviations in the detector and normalizing pixel element response by comparison of the response signals generated while varying the calibration signal intensity and acquisition time; and applying the systematic signal deviations and the pixel normalization to a measured raw data corresponding to the emitted signal from the biological sample wherein the response signals that yield the systematic signal deviations and the pixel normalization are obtained in a similar condition as that of the measured raw data.

2. The method of claim 1, further comprising directing the calibration signal towards the detector such that each of the plurality of pixel elements is exposed to the calibration signal in a substantially uniform manner for the acquisition time.

3. The method of claim 1, wherein the variations in calibration signal intensity comprise a first and second signal intensity and wherein the variations in pixel element acquisition time comprise a first and second signal acquisition time thereby allowing determination of four or less components of a given response signal.

4. The method of claim 3, wherein the first signal intensity comprises a substantially uniform non-zero intensity and wherein the second signal intensity comprises a substantially nil intensity.

5. The method of claim 4, wherein the first signal acquisition time comprises a long signal acquisition time and wherein the second signal acquisition time comprises a short signal acquisition time, wherein the long acquisition time is greater than the short acquisition time.

6. The method of claim 5, wherein the four components of a given response signal comprises:
   (a) a first component that depends on both the calibration signal intensity and the acquisition time;
   (b) a second component that depends on the calibration signal intensity but not on the acquisition time;
   (c) a third component that depends on the acquisition time but not on the calibration signal intensity; and
   (d) a fourth component that depends neither on the calibration signal intensity or the acquisition time.

7. The method of claim 6, wherein the first component comprises a baseline component suitable for flat-field correction.

8. The method of claim 7, wherein the second component comprises a contribution to the response signal when the calibration signal intensity transitions from the non-zero intensity to the substantially nil intensity.

9. The method of claim 8, wherein the third component comprises a dark signal component.

10. The method of claim 9, wherein the fourth component comprises a contribution to the response signal during an idle period following the acquisition time.

11. The method of claim 10, wherein applying the systematic signal deviations and the pixel normalization comprises:
   (a) subtracting the idle period contribution from the measured raw data to yield a first adjusted data for a given pixel;
   (b) subtracting the dark signal component from the first adjusted data to yield a second adjusted data for the pixel;
   (c) removing the calibration signal intensity transition contribution from the second adjusted data to yield a third adjusted data for the pixel; and
   (d) normalizing the third adjusted data of the given pixel relative to other pixels by comparing the given pixel's baseline component to that of the other pixels wherein the normalization of the third adjusted data yields a fourth adjusted data.

12. The method of claim 10, wherein identifying systematic signal deviations comprises:
   (a) obtaining, for each pixel, measured raw data comprising a baseline long signal value $A_{BL}$ during a known long measurement frame duration $T_{PL}$, a baseline short signal value $A_{BS}$ during a known short measurement flame duration $T_{PS}$, a dark long signal value $A_{DL}$ during another $T_{PL}$, and a dark short signal value $A_{DS}$ during another $T_{PS}$;
   (b) determining, for each pixel, signal values $W_{ie}$ and $W_{DC}$ corresponding to the baseline component and the dark signal component respectively, based on the measured and known values $A_{BL}$, $A_{BS}$, $A_{DL}$, $A_{DS}$, $T_{PL}$, and $T_{PS}$;
   (c) determining, for each pixel having indices ij, time durations $T_L$, $T_S$, $T_{idle}$, and $T_{ns}^{ij}$ corresponding to time values of long acquisition time, short acquisition time, idle time, and the calibration signal intensity transition time, respectively, based on the determined or known values $A_{BL}$, $A_{BS}$, $A_{DL}$, $A_{DS}$, $T_{PL}$, $T_{PS}$, and a ratio of long and short acquisition times; and
   (d) determining, for each pixel, the calibration signal components based on the determined or known values $A_{BL}$, $A_{BS}$, $A_{DL}$, $A_{DS}$, $T_{PL}$, $T_{PS}$, $T_{Lo}$ $T_S$, $T_{idle}$, $T_{ns}^{ij}$, $W_{ie}$, and $W_{DC}$.

13. The method of claim 12, wherein determining the signal values $W_{ie}$ and $W_{DC}$ comprise:
   (a) $W_{ie}=[(A_{BL}-A_{BS})-(A_{DL}-A_{DS})]/(T_{PL}-T_{PS})$; and
   (b) $W_{DC}=(A_{DL}-A_{DS})/(T_{PL}-T_{PS})$.

14. The method of claim 12, wherein determining time durations $T_L$, $T_S$, $T_{idle}$, and $T_{ns}^{ij}$ comprise:
   (a) $T_L=n(T_{PL}-T_{PS})/(n-1)$ where n is representative of a ratio of long and short acquisition times;
   (b) $T_S=T_L-(T_{PL}-T_{PS})$;
   (c) $T_{idle}=(nT_{PS}-T_{PL})/(n-1)$; and
   (d) $T_{ns}^{ij}=(n-m^{ij})T_{PL}-T_{PS})/[(m^{ij}-1)(n-1)]$ where $m^{ij}=(A_{BL}-A_{DL})/(A_{BS}-A_{DS})$.

15. The method of claim 12, wherein determining the calibration components includes:
   (a) $A_{L1}=W_{ie} T_L$ is representative of the long baseline component suitable for flat-field correction;
   (b) $A_{S1}=W_{ie} T_S$ is representative of the short baseline component;
   (c) $A_2=W_{ie} T_{ns}^{ij}$ is representative of the contribution during the calibration signal intensity transition time for both long and short acquisition times;
   (d) $A_{L3}=W_{DC} T_L$ is representative of the dark signal component during the long acquisition time;
   (e) $A_{S3}=W_{DC} T_S$ is representative of the dark signal component during the short acquisition time; and
   (f) $A_2=A_{DL}-A_{L3}$ is representative of the contribution during the idle time.

16. A system for performing a biological assay, comprising:
   a biological sample configured to emit signals;
   a detector comprising a plurality of pixel elements configured to resolve the emitted signals from the biological sample;
   a processor configured to acquire and evaluate response signals from the pixel elements generated by each of the pixel elements resulting from exposure to a calibration signal while varying an intensity of the calibration signal in combination with varying of an acquisition time of the pixel elements; wherein the processor is configured to identify systematic signal deviations in the detector and normalize pixel element response by comparison of the response signals generated while varying the calibration signal intensity and acquisition time and wherein the processor applies the systematic signal deviations and the pixel normalization to a measured raw data corresponding to the emitted signal from the biological sample wherein the response signals that yield the systematic signal deviations and the pixel normalization are obtained in a similar condition as that of the measured raw data.

17. The system of claim 16, further comprising a calibration component that is configured to direct the calibration signal towards the detector such that each of the plurality of pixel elements is exposed to the calibration signal in a substantially uniform manner for the acquisition time to generate the response signals.

18. The system of claim 16, wherein the variations in calibration signal intensity comprise a first and second signal intensity and wherein the variations in pixel element acquisition time comprise a first and second signal acquisition time thereby allowing determination of four or less components of a given response signal.

19. The system of claim 18, wherein the first signal intensity comprises a substantially uniform non-zero intensity and wherein the second signal intensity comprises a substantially nil intensity.

20. The system of claim 19, wherein the first signal acquisition time comprises a long signal acquisition time and wherein the second signal acquisition time comprises a short signal acquisition time, wherein the long acquisition time is greater than the short acquisition time.

21. The system of claim 20, wherein the four components of a given response signal comprises:
    (a) a first component that depends on both the calibration signal intensity and the acquisition time;
    (b) a second component that depends on the calibration signal intensity but not on the acquisition time;
    (c) a third component that depends on the acquisition time but not on the calibration signal intensity; and
    (d) a fourth component that depends neither on the calibration signal intensity or the acquisition time.

22. The system of claim 21, wherein the first component comprises a baseline component suitable for flat-field correction.

23. The system of claim 22, wherein the second component comprises a contribution to the response signal when the calibration signal intensity transitions from the non-zero intensity to the substantially nil intensity.

24. The system of claim 23, wherein the third component comprises dark signal component.

25. The system of claim 24, wherein the fourth component comprises a contribution to the response signal during an idle period following the acquisition time.

26. The system of claim 25, wherein the processor applies the systematic signal deviations and the pixel normalization by:
    (a) subtracting the idle period contribution from the measured raw data to yield a first adjusted data for a given pixel;
    (b) subtracting the dark signal component from the first adjusted data to yield a second adjusted data for the pixel;
    (c) removing the calibration signal intensity transition contribution from the second adjusted data to yield a third adjusted data for the pixel; and
    (d) normalizing the third adjusted data of the given pixel relative to other pixels by comparing the given pixel's baseline component to that of the other pixels wherein the normalization of the third adjusted data yields a fourth adjusted data.

27. The system of claim 25, wherein the processor identifies the systematic signal deviations by:
    (a) obtaining, for each pixel, measured raw data comprising a baseline long signal value $A_{BL}$ during a known long measurement frame duration $T_{PL}$, a baseline short signal value $A_{BS}$ during a known short measurement frame duration $T_{PS}$, a dark long signal value $A_{DL}$ during another $T_{PL}$, and a dark short signal value $A_{DS}$ during another $T_{PS}$;
    (b) determining, for each pixel, signal values $W_{ie}$ and $W_{DC}$ corresponding to the baseline component and the dark signal component respectively, based on the measured and known values $A_{BL}$, $A_{BS}$, $A_{DL}$, $A_{DS}$, $T_{PL}$, and $T_{PS}$;
    (c) determining, for each pixel having indices ij, time durations $T_L$, $T_S$, $T_{idle}$, and $T_{ns}^{ij}$ corresponding to time values of long acquisition time, short acquisition time, idle time, and the calibration signal intensity transition time, respectively, based on the determined or known values $A_{BL}$, $A_{BS}$, $A_{DL}$, $A_{DS}$, $T_{PL}$, $T_{PS}$, and a ratio of long and shod acquisition times; and
    (d) determining, for each pixel, the calibration signal components based on the determined or known values $A_{BL}$, $A_{BS}$, $A_{DL}$, $A_{DS}$, $T_{PL}$, $T_{PS}$, $T_L$, $T_S$, $T_{idle}$, $T_{ns}^{ij}$, $W_{ie}$, and $W_{DC}$.

28. The system of claim 27, wherein the processor determines the signal values $W_{ie}$ and $W_{DC}$ by:
    (a) $W_{ie}=[(A_{BL}-A_{BS})-(A_{DL}-A_{DS})]/(T_{PL}-T_{PS})$; and
    (b) $W_{DC}=(A_{DL}-A_{DS})/(T_{PL}-T_{PS})$.

29. The system of claim 27, wherein the processor determines the time durations $T_L$, $T_S$, $T_{idle}$, and $T_{ns}^{ij}$ by:
    (a) $T_L=n(T_{PL}-T_{PS})/(n-1)$ where n is representative of a ratio of long and short acquisition times;
    (b) $T_S=T_L-(T_{PL}-T_{PS})$;
    (c) $T_{idle}^{ij}=(nT_{PS}-T_{PL})/(n-1)$; and
    (d) $T_{ns}^{ij}=(n-m^{ij})T_{PL}-T_{PS})/[(m^{ij}-1)(n-1)]$ where $m^{ij}=(A_{BL}-A_{DL})/(A_{BS}-A_{DS})$.

30. The system of claim 27, wherein the processor determines at least some of the calibration components by:
    (a) $A_{L1}=W_{ie}\ T_L$ is representative of the long baseline component suitable for flat-field correction;
    (b) $A_{S1}=W_{ie}\ T_S$ is representative of the short baseline component;
    (c) $A_2=W_{ie}\ T_{ns}^{ij}$ is representative of the contribution during the calibration signal intensity transition time for both long and short acquisition times;
    (d) $A_{L3}=W_{DC}\ T_L$ is representative of the dark signal component during the long acquisition time;
    (e) $A_{S3}=W_{DC}\ T_S$ is representative of the dark signal component during the short acquisition time; and
    (f) $A_2=A_{DL}-A_{L3}$ is representative of the contribution during the idle time.

31. A system for characterizing a detector for a biological analyzer, comprising:
    a processor configured to acquire and evaluate response signals from the detector resulting from exposure to a calibration signal while varying the intensity of the calibration signal in combination with, varying of acquisition tune of the detector;
    wherein the processor is configured to resolve the response signals, based on the variations in the intensity of the calibration signal and the acquisition time, into two or more components that contribute to the response signals.

32. The system, of claim 31, further comprising a calibration component that is configured to direct the calibration signal towards the detector such that at least a portion of the detector is exposed to the calibration signal in a substantially uniform manner for the acquisition time to generate the response signals.

33. The system of claim 31, wherein the detector comprises a plurality of pixel elements.

34. The system of claim 33, wherein a portion of the plurality of pixel elements are characterized.

35. The system of claim 33, wherein substantially all of the plurality of pixel elements are characterized.

36. The system of claim 33, wherein the detector comprises a charge coupled device.

37. The system of claim 33, wherein the response signal from the detector comprises a plurality of signals corresponding to the plurality of pixels.

38. The system of claim 37, wherein each pixel is characterized by resolving its corresponding signal.

39. The system of claim 37, wherein the plurality of pixels are grouped into bins, so that a signal from each bin represents a combination of signals from the pixels in that bin.

40. The system of claim 31, wherein the variations in calibration signal intensity comprise a first and a second signal intensity and wherein the variations in detector acquisition time comprise a first and a second signal acquisition time thereby allowing determination of two to four components of a given response signal.

41. The system of claim 40, wherein the first signal intensity comprises a substantially uniform non-zero intensity and wherein the second signal intensity comprises a substantially nil intensity.

42. The system of claim 41, wherein the first acquisition time comprises a long signal acquisition time and wherein the second acquisition time comprises a short signal acquisition time, wherein the long acquisition time is greater than the short acquisition time.

43. The system of claim 42, wherein four components are resolved for a given response signal, said four components comprising:
   (a) a first component that depends on both the calibration signal intensity and the acquisition time;
   (b) a second component that depends on the calibration signal intensity but not on the acquisition time;
   (c) a third component that depends on the acquisition time but not on the calibration signal intensity; and
   (d) a fourth component that depends neither on the calibration signal intensity or the acquisition time.

44. The system of claim 43, wherein the first component comprises a baseline component.

45. The system of claim 43, wherein the second component comprises a contribution to the response signal when the calibration signal intensity transitions from to non-zero intensity to the substantially nil intensity.

46. The system of claim 43, wherein the third component comprises a dark signal component.

47. The system of claim 43, wherein the fourth component comprises a contribution to the response signal during an idle period following the acquisition time.

48. A method characterizing a detector for a biological analyzer, the method comprising:
   evaluating a response signal while varying an intensity of a calibration signal in combination with varying of an acquisition time; and
   resolving the response signal based on the variations in the intensity of the calibration signal and the acquisition time, into two or more components that contribute to the response signal.

49. The method of claim 48, further comprising directing the calibration signal towards the detector such that at least a portion of the detector is exposed to the calibration signal in a substantially uniform manner for the acquisition time to generate the response signal.

50. The method of claim 48, wherein varying the intensity of the calibration signal comprises providing a first and a second signal intensity and wherein varying the acquisition time comprises providing a first and a second signal acquisition time thereby allowing determination of two to four components of a given response signal.

51. The method of claim 50, wherein the first signal intensity comprises a substantially uniform non-zero intensity and wherein the second signal intensity comprises a substantially nil intensity.

52. The method of claim 51, wherein the first acquisition time comprises a long signal acquisition time and wherein the second acquisition time comprises a short signal acquisition time, wherein the long acquisition time is greater than the short acquisition time.

53. The method of claim 52, wherein four components are resolved for a given response signal, said four components comprising:
   (a) a first component that depends on both the calibration signal intensity and the acquisition time;
   (b) a second component that depends on the calibration signal intensity but not on the acquisition time;
   (c) a third component that depends on the acquisition time but not on the calibration signal intensity; and
   (d) a fourth component that depends neither on the calibration signal intensity or the acquisition time.

54. The method of claim 53, wherein the first component comprises a baseline component.

55. The method of claim 53, wherein the second component comprises a contribution to the response signal when the calibration signal intensity transitions from the non-zero intensity to the substantially nil intensity.

56. The method of claim 53, wherein the third component comprises a dark signal component.

57. The method of claim 53, wherein the fourth component comprises a contribution to the response signal during an idle period following the acquisition time.

* * * * *